(12) United States Patent
Suzuki et al.

(10) Patent No.: US 10,893,800 B2
(45) Date of Patent: Jan. 19, 2021

(54) BINOCULAR MEASUREMENT DEVICE, BINOCULAR MEASUREMENT METHOD, AND BINOCULAR MEASUREMENT PROGRAM

(71) Applicant: HAMAMATSU PHOTONICS K.K., Hamamatsu (JP)

(72) Inventors: Kazutaka Suzuki, Hamamatsu (JP);
Munenori Takumi, Hamamatsu (JP);
Naotoshi Hakamata, Hamamatsu (JP);
Haruyoshi Toyoda, Hamamatsu (JP);
Yoshinori Matsui, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 179 days.

(21) Appl. No.: 15/575,856

(22) PCT Filed: Mar. 30, 2016

(86) PCT No.: PCT/JP2016/060517
§ 371 (c)(1),
(2) Date: Nov. 21, 2017

(87) PCT Pub. No.: WO2016/189966
PCT Pub. Date: Dec. 1, 2016

(65) Prior Publication Data
US 2018/0125357 A1 May 10, 2018

(30) Foreign Application Priority Data
May 28, 2015 (JP) .................. 2015-108367

(51) Int. Cl.
*A61B 3/14* (2006.01)
*A61B 3/113* (2006.01)
(Continued)

(52) U.S. Cl.
CPC ............ *A61B 3/113* (2013.01); *A61B 3/0025* (2013.01); *A61B 3/112* (2013.01); *A61B 3/145* (2013.01);
(Continued)

(58) Field of Classification Search
CPC ....... A61B 3/0025; A61B 3/112; A61B 3/113; A61B 3/145; A61B 3/005; A61B 3/0091;
(Continued)

(56) References Cited

U.S. PATENT DOCUMENTS

| 5,936,663 A | * | 8/1999 | Tabata | ............... G02B 27/0093 348/51 |
| 2009/0103050 A1 | * | 4/2009 | Michaels | ............. A61B 3/0075 351/208 |

FOREIGN PATENT DOCUMENTS

| JP | H07-303608 A | 11/1995 |
| JP | H09-175224 A | 7/1997 |

(Continued)

OTHER PUBLICATIONS

International Preliminary Report on Patentability dated Dec. 7, 2017 for PCT/JP2016/060517.

(Continued)

*Primary Examiner* — Brandi N Thomas
(74) *Attorney, Agent, or Firm* — Faegre Drinker Biddle & Reath LLP

(57) ABSTRACT

An object is to simply and easily evaluate differences in behavior of the eyes of subjects. A binocular measurement system 1 includes a photodetector 7 that detects reflected light from the right eye $E_R$ and the left eye $E_L$ of a subject, and outputs image signal of the reflected light, a feature amount calculating unit 11 that calculates a feature amount corresponding to the right eye $E_R$ and a feature amount corresponding to the left eye $E_L$ based on the image signal, (Continued)

and a comparison value calculating unit 13 that calculates, based on the two feature amounts, a comparison value obtained by comparing the two feature amounts.

7 Claims, 28 Drawing Sheets

(51) Int. Cl.

| | |
|---|---|
| *A61B 3/11* | (2006.01) |
| *G06K 9/00* | (2006.01) |
| *G06K 9/62* | (2006.01) |
| *A61B 3/00* | (2006.01) |
| *G06F 3/03* | (2006.01) |
| *A61B 3/08* | (2006.01) |

(52) U.S. Cl.
CPC ....... *G06F 3/0304* (2013.01); *G06K 9/00248* (2013.01); *G06K 9/00604* (2013.01); *G06K 9/6215* (2013.01); *A61B 3/08* (2013.01)

(58) Field of Classification Search
CPC .... A61B 3/02; A61B 3/08; A61B 3/11; A61B 5/16; A61B 5/163; A61B 5/165; A61B 3/00; A61B 3/085; A61B 3/10; A61B 3/14; A61B 3/152

USPC ........ 351/200, 205–206, 209–211, 221–223, 351/243–246
See application file for complete search history.

(56) References Cited

FOREIGN PATENT DOCUMENTS

| | | |
|---|---|---|
| JP | 2008-246143 A | 10/2008 |
| JP | 2012-196328 A | 10/2012 |

OTHER PUBLICATIONS

Engbert, R., "Microsaccades: a microcosm for research on oculomotor control, attention, and visual perception," Martinez-Conde, Macknik, Martinez, Alonso & Tse (Eds.) Profress in Brain Research, 2006, vol. 154, pp. 177-192.

Niida, Takahiro, "Neuro-ophthalmology Introduction Series 96 Eyelid blink 2 Eyeblink," Neuro-ophthalmol.Jpn., 2012, vol. 29, No. 2, pp. 204-212, including English translation.

* cited by examiner

*Fig.5*
(a)
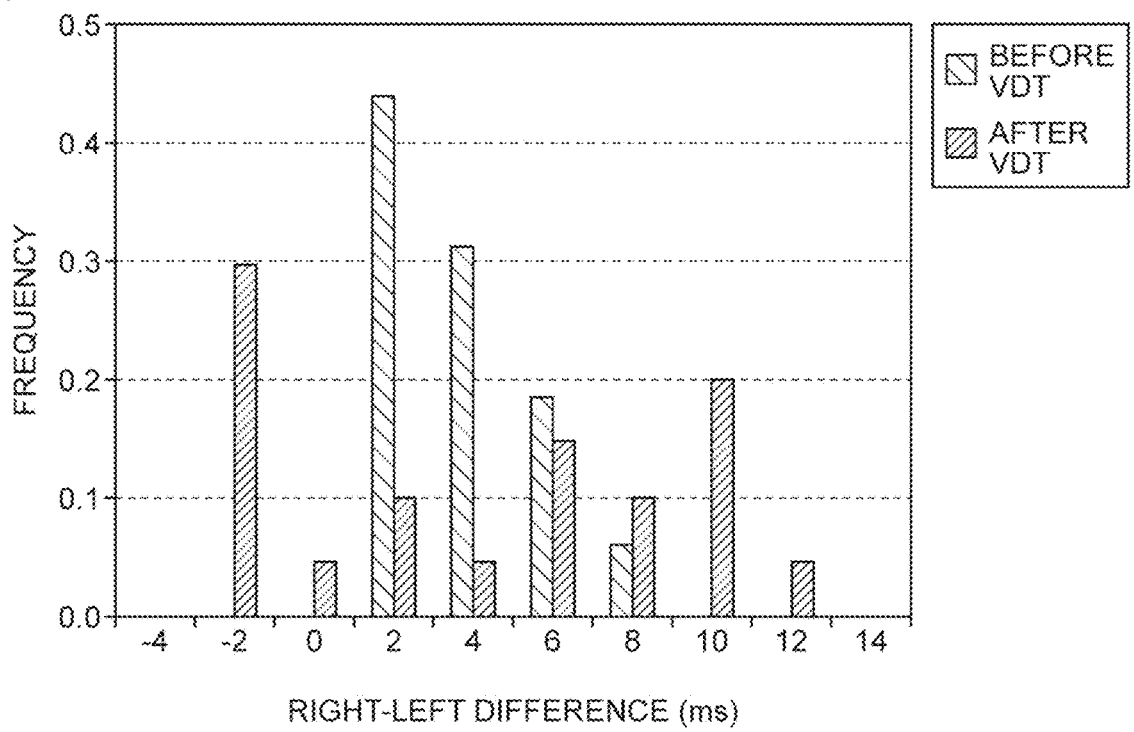
(b)
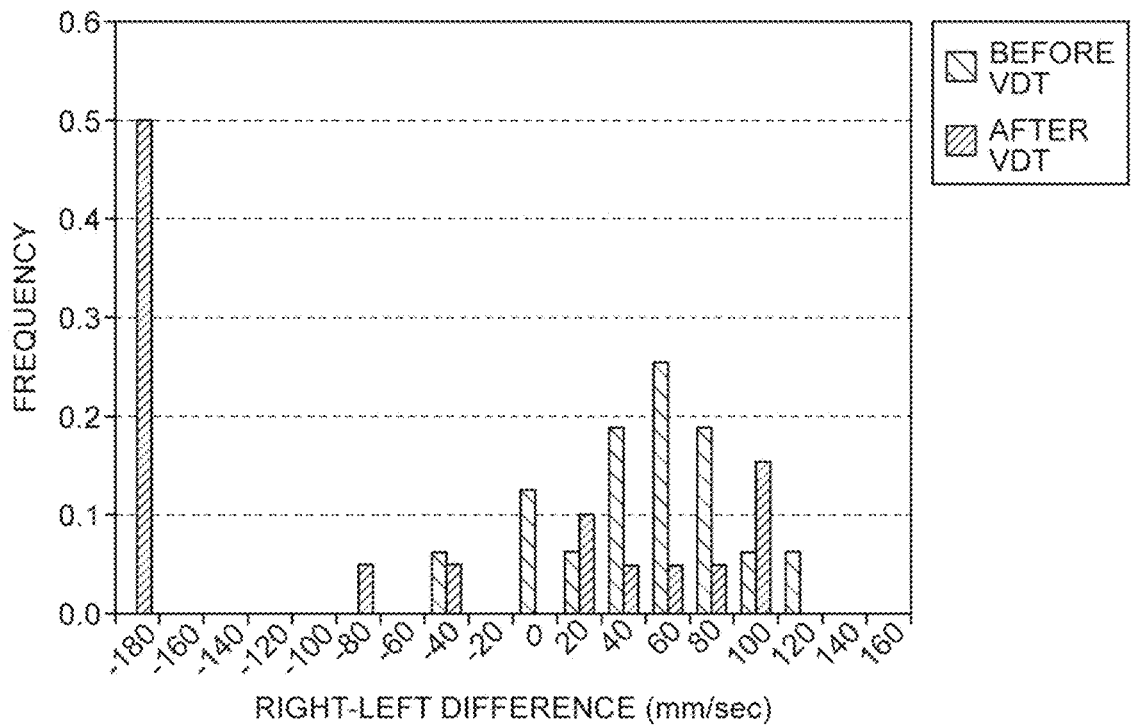

Fig.6
(a)
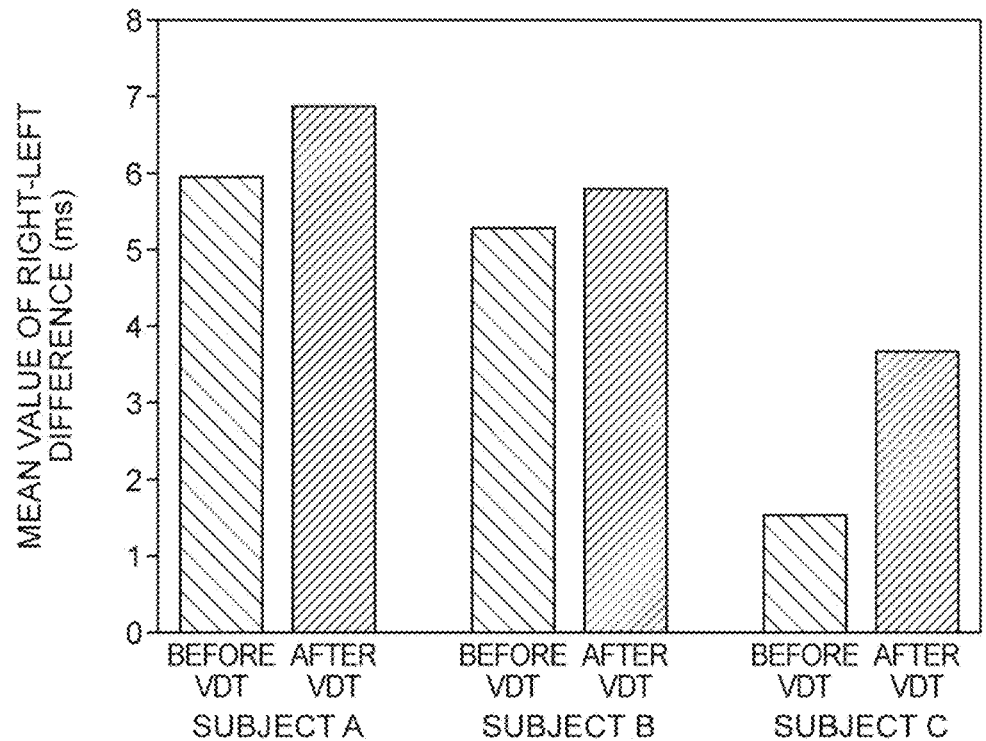
(b)
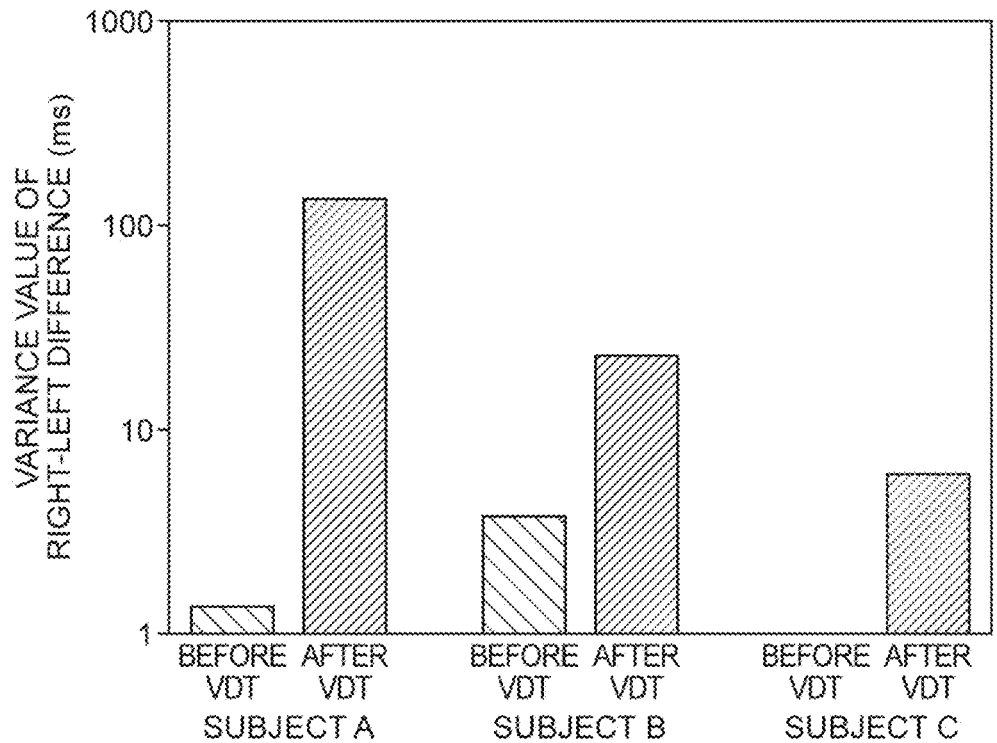

Fig.7
(a)
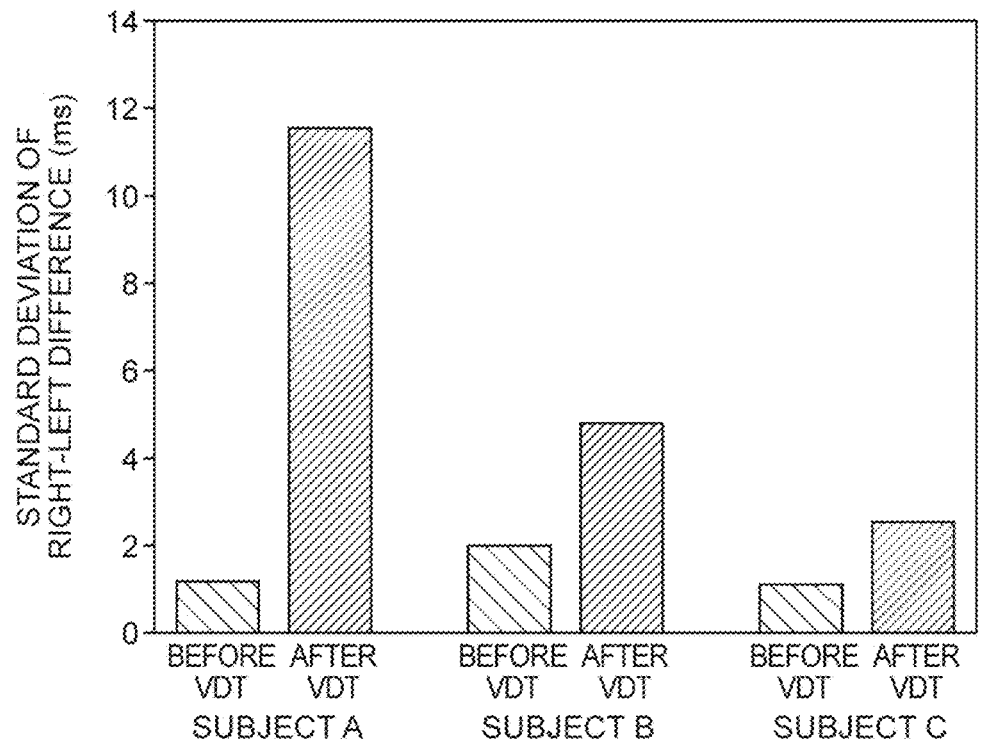
(b)
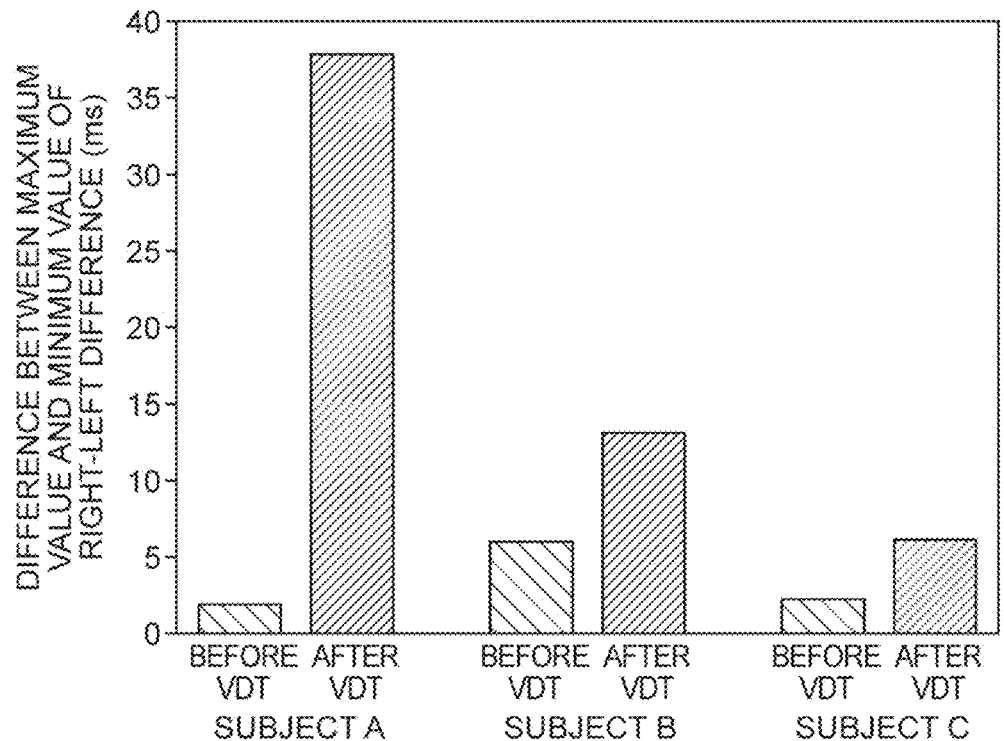

*Fig.8*
(a)
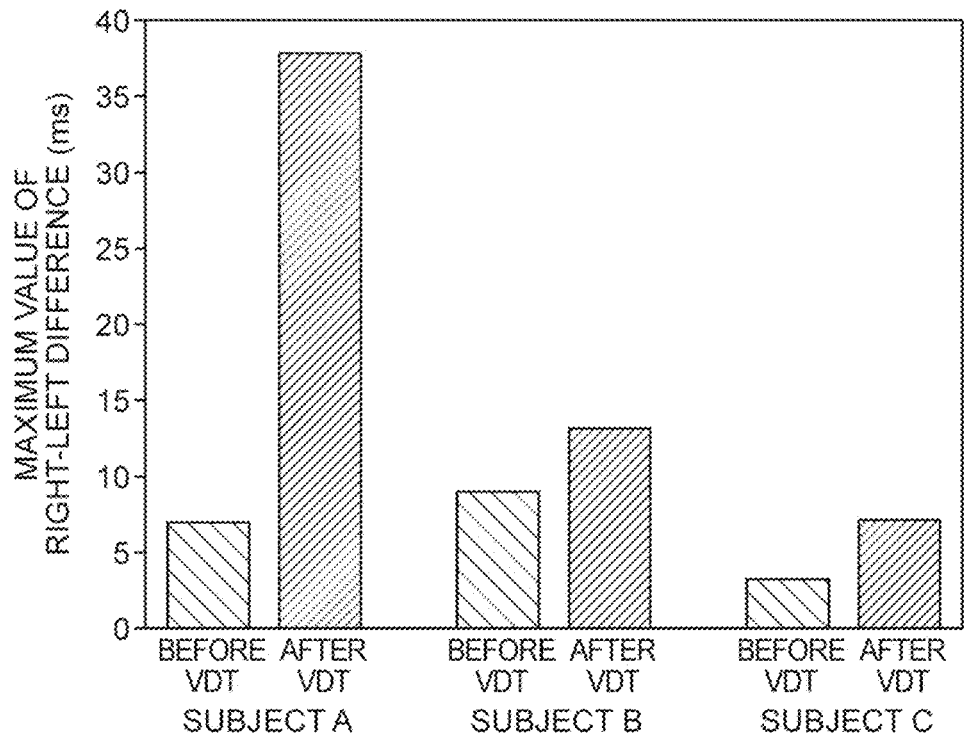
(b)
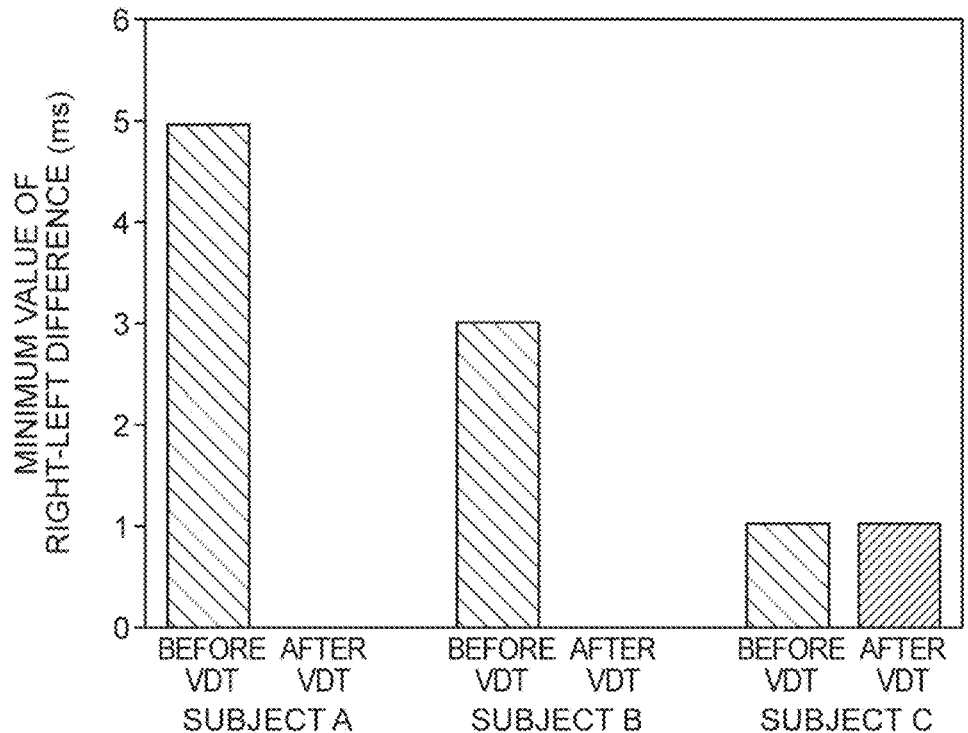

*Fig.9*
(a)
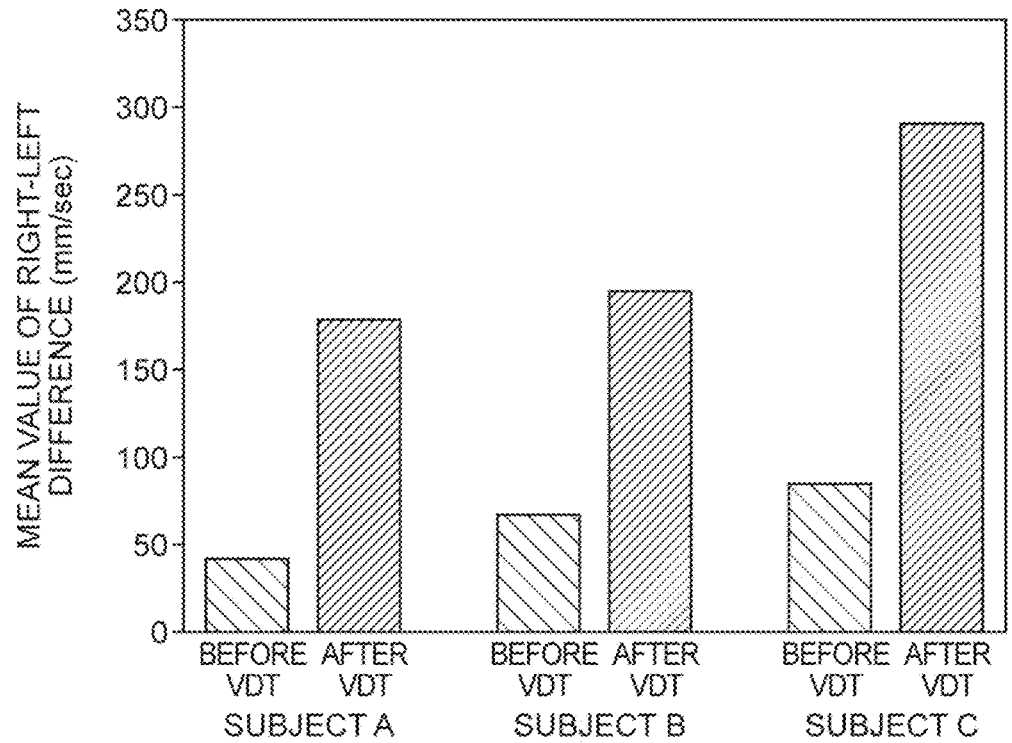
(b)
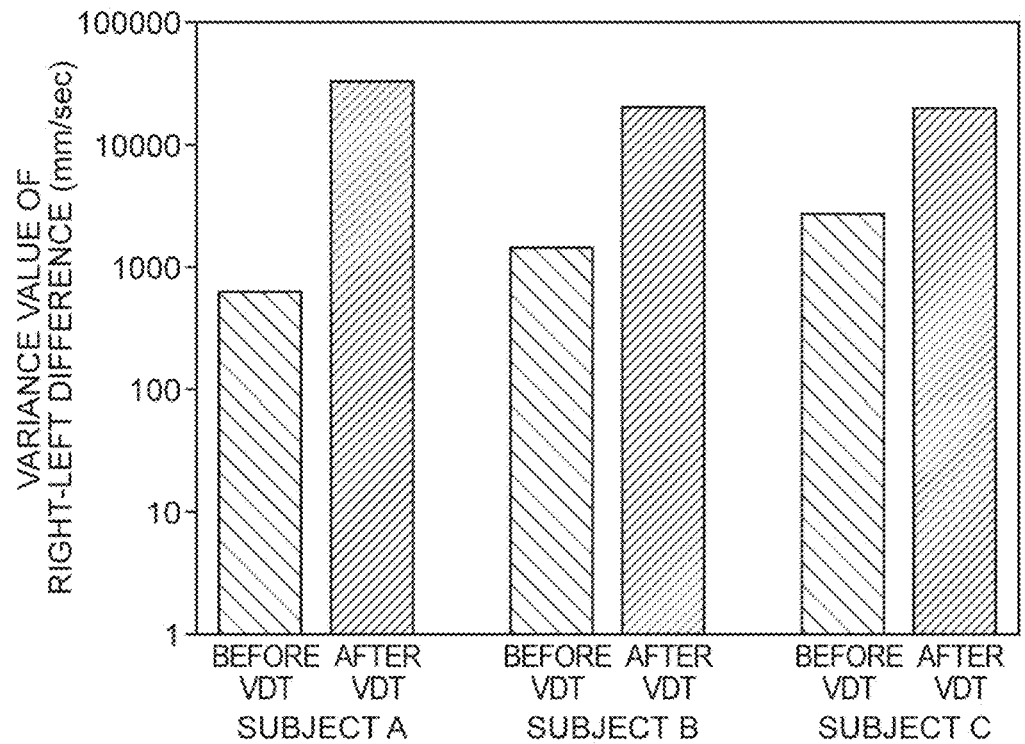

*Fig.10*
(a)
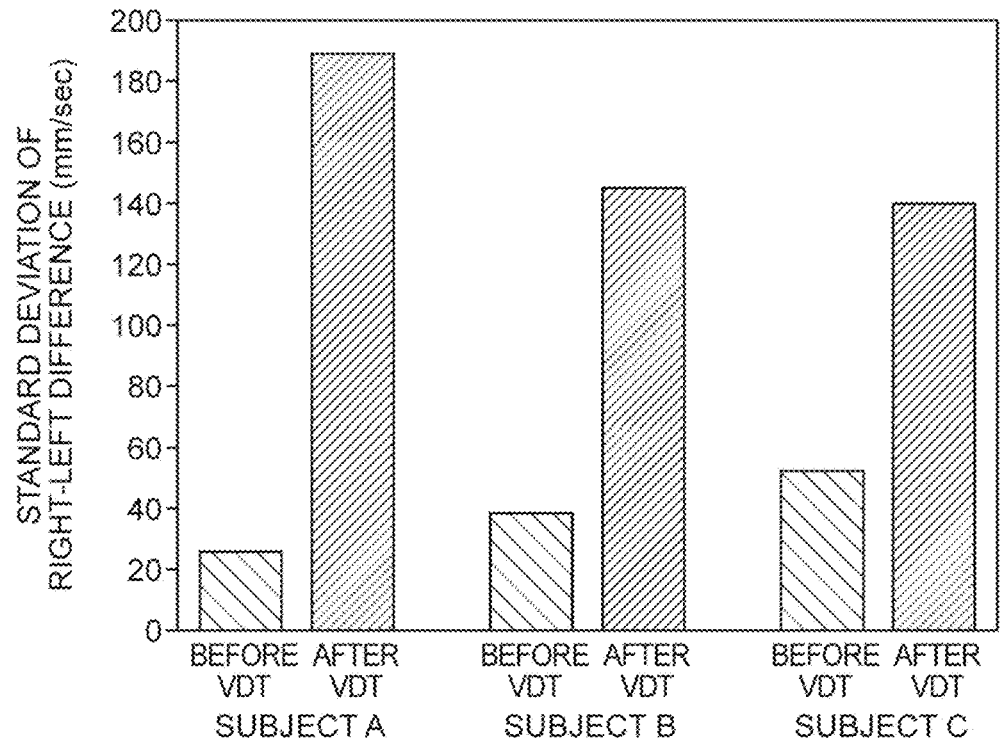
(b)
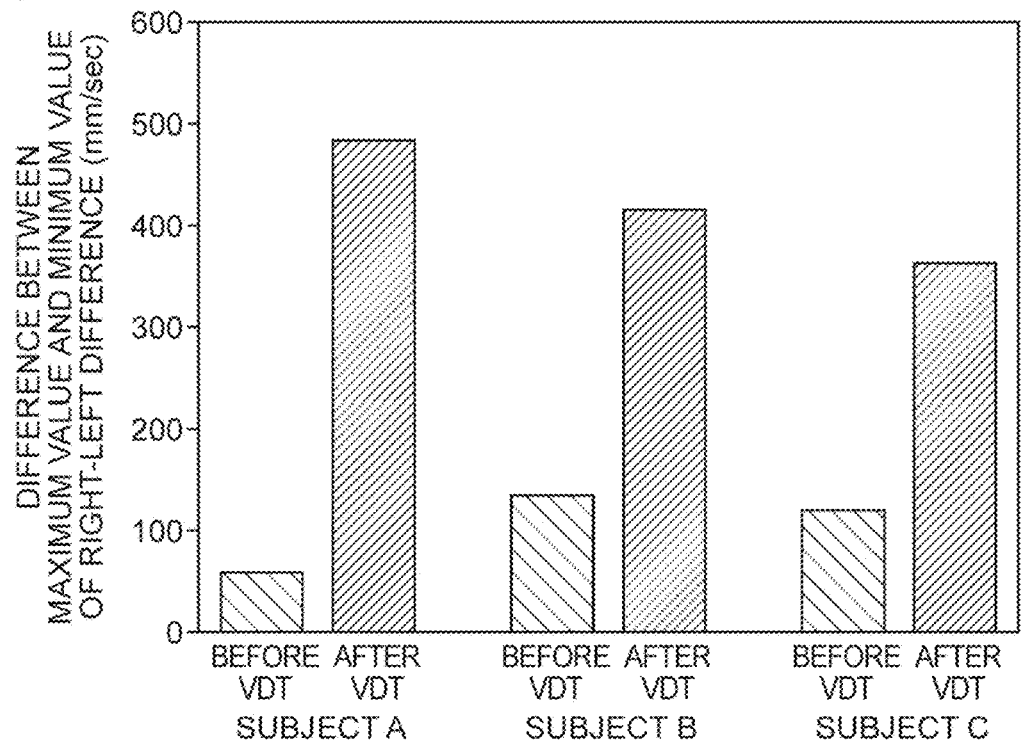

Fig.11
(a)
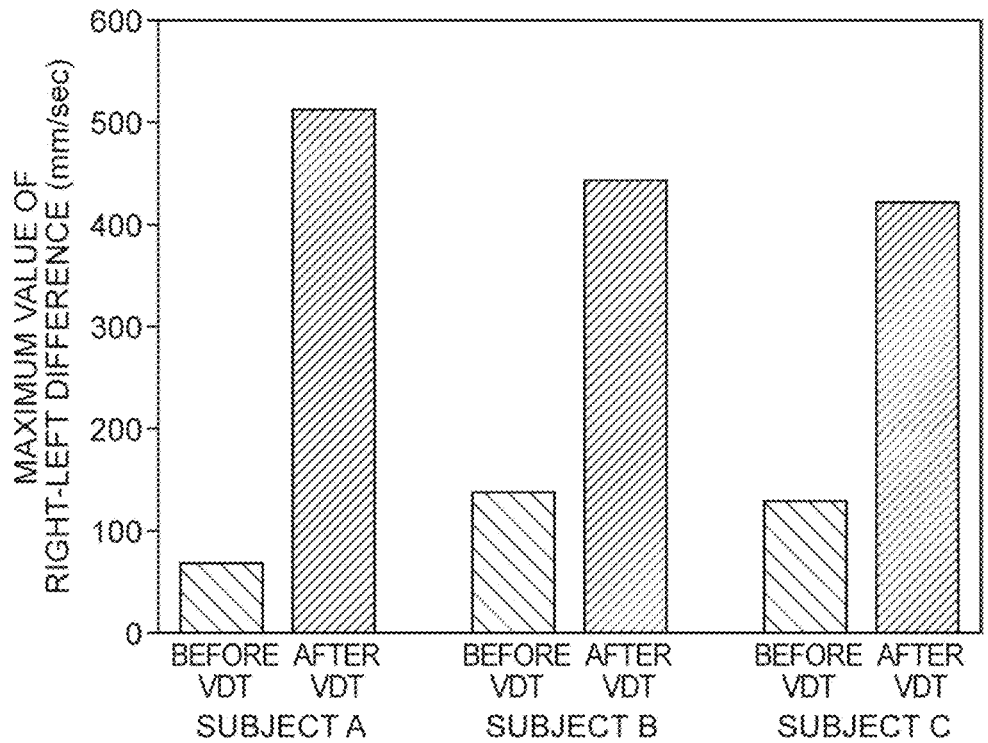
(b)
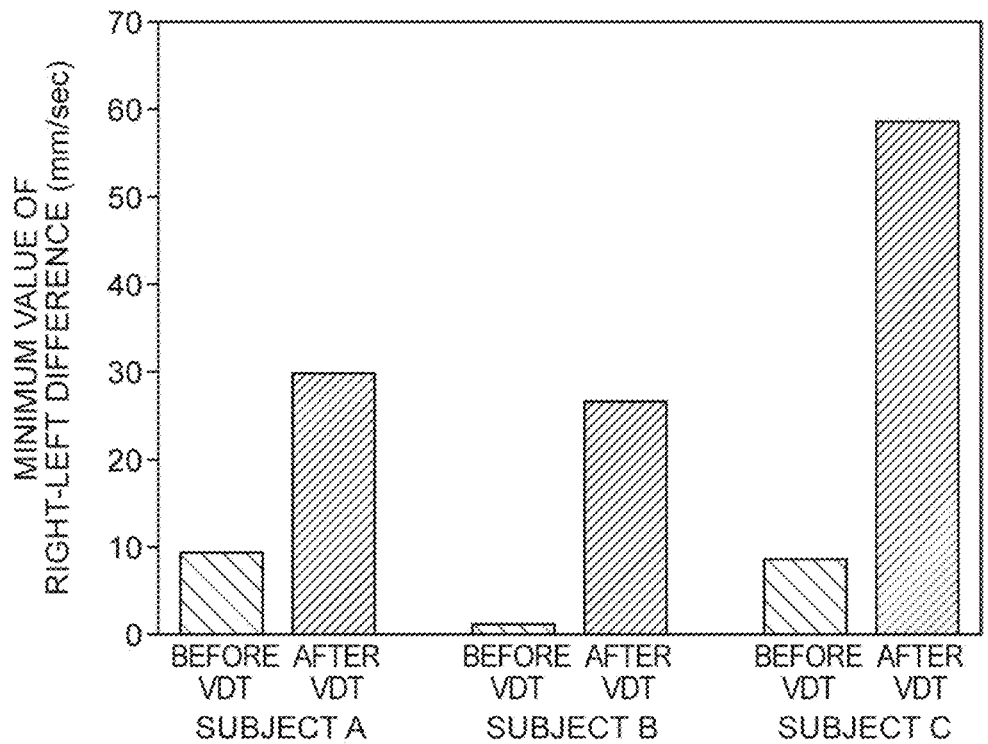

Fig.12
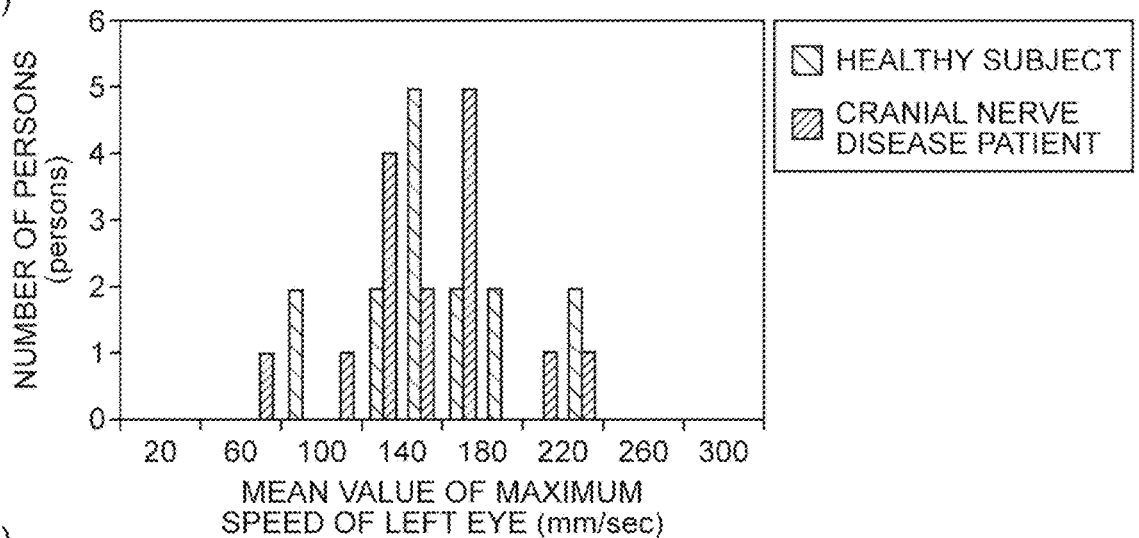
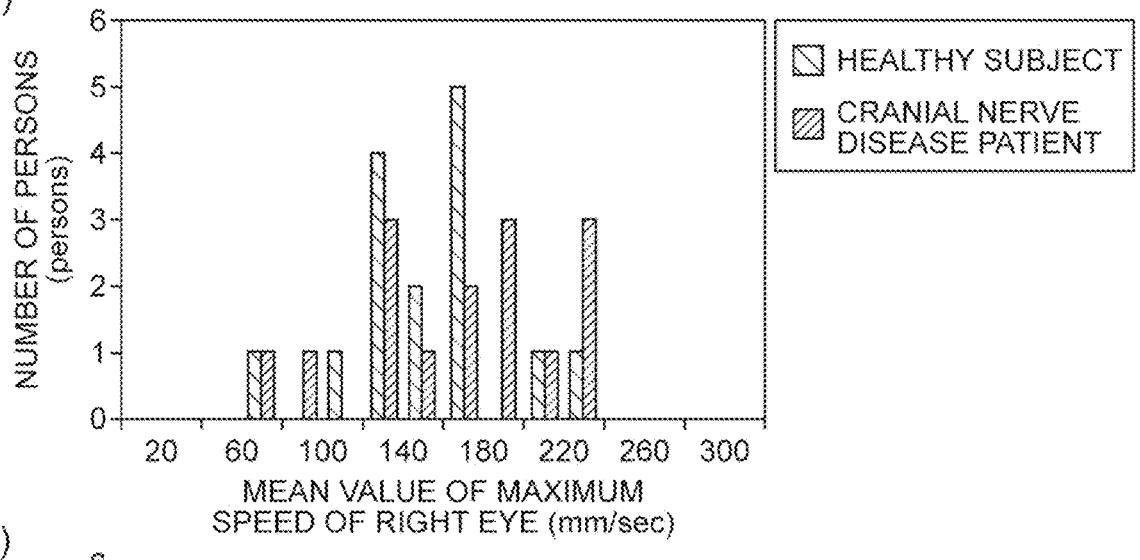
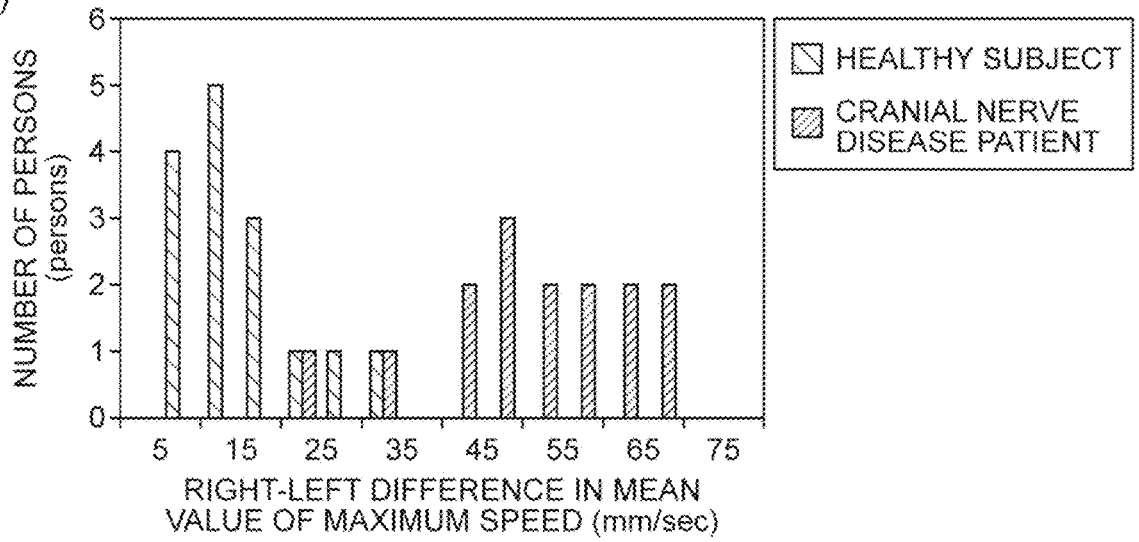

*Fig.13*
(a)
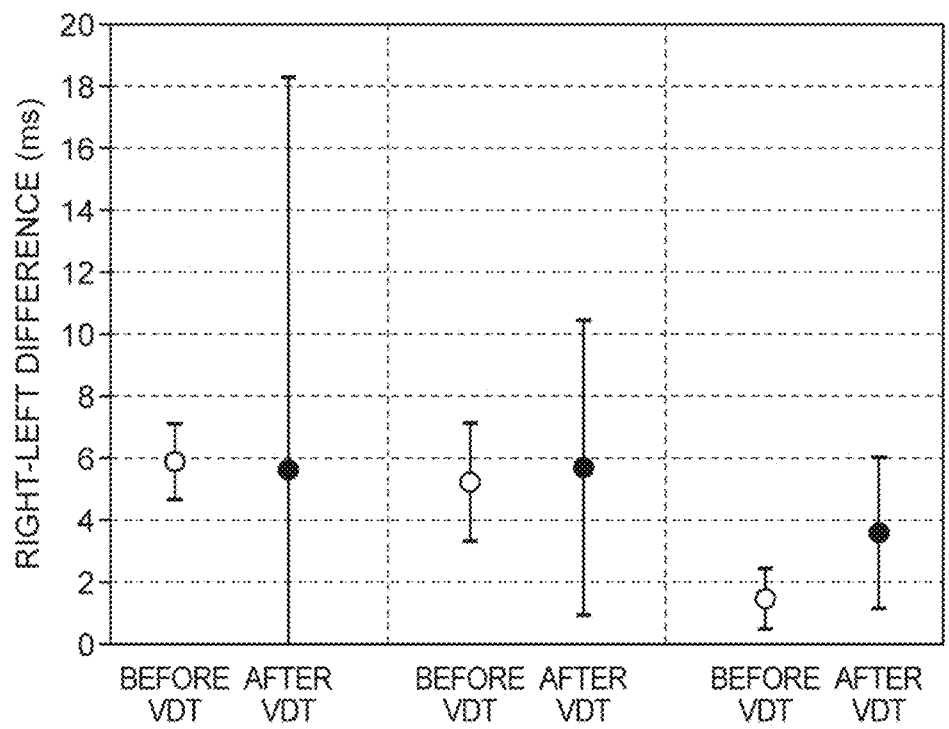
(b)
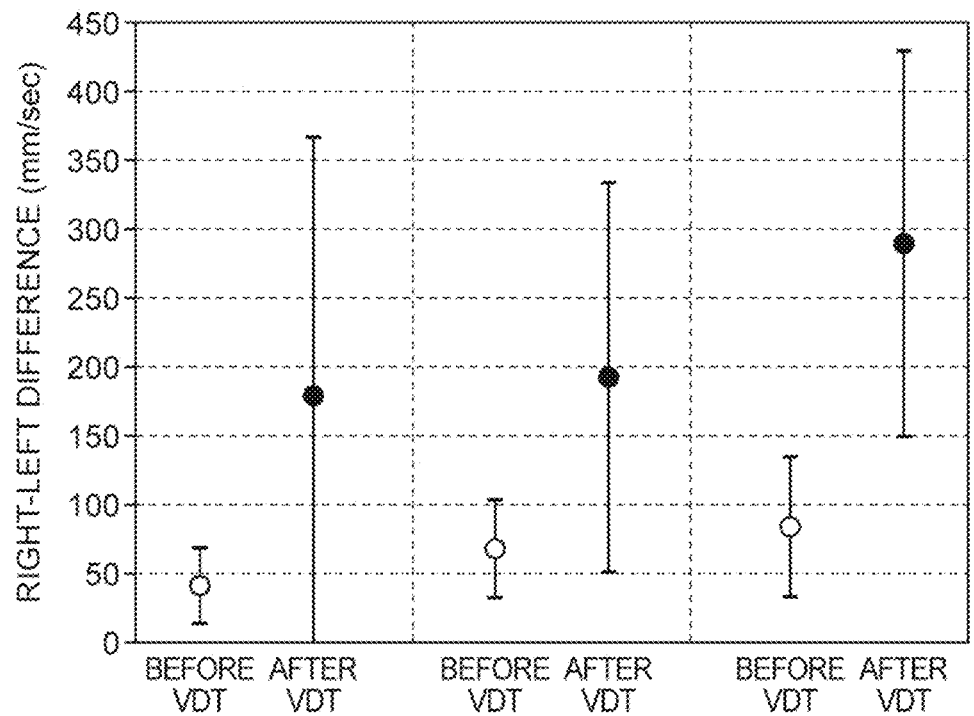

Fig.15
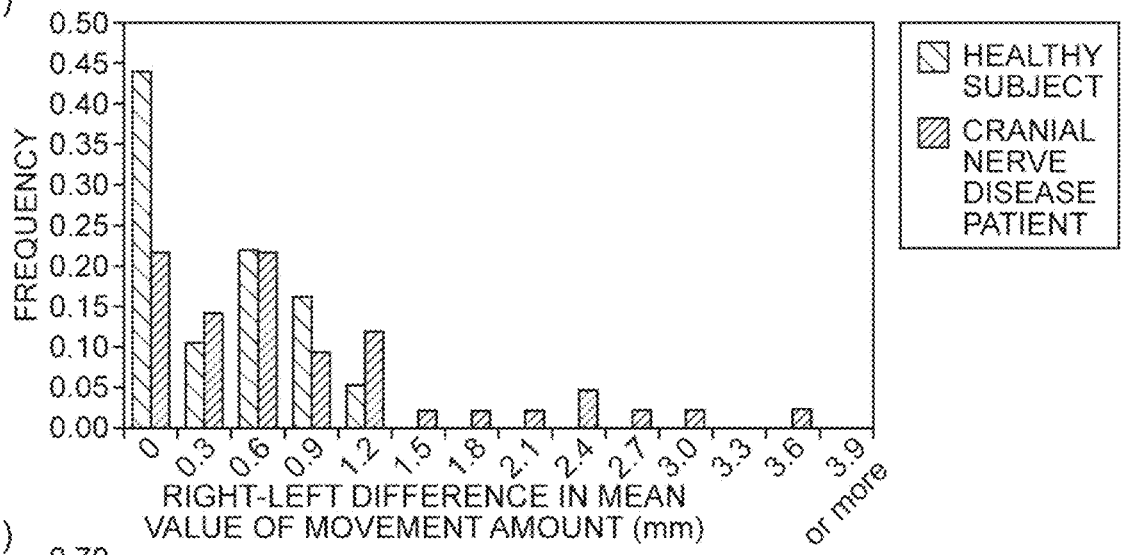
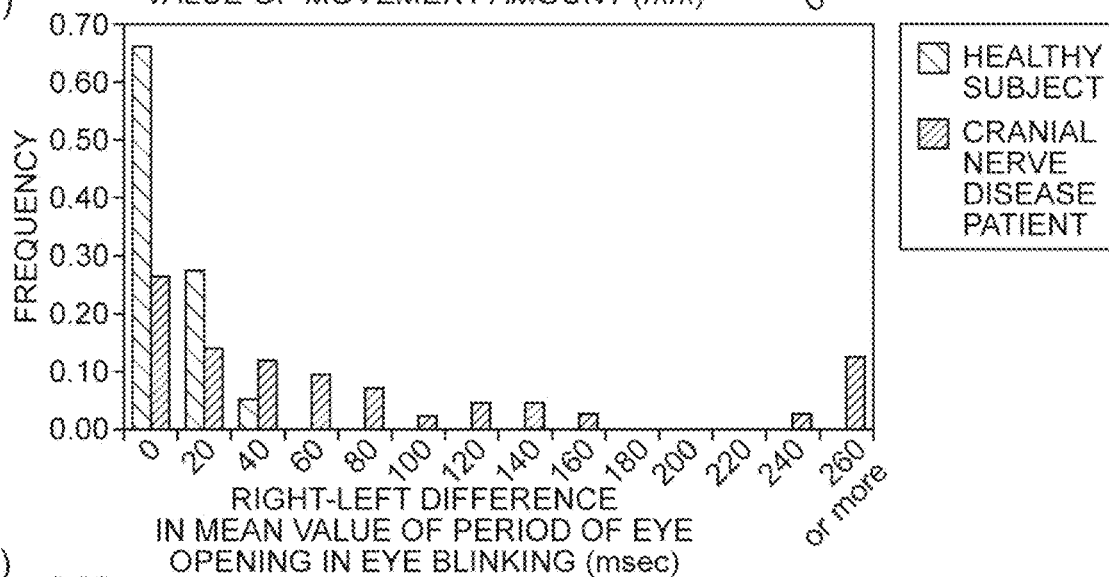
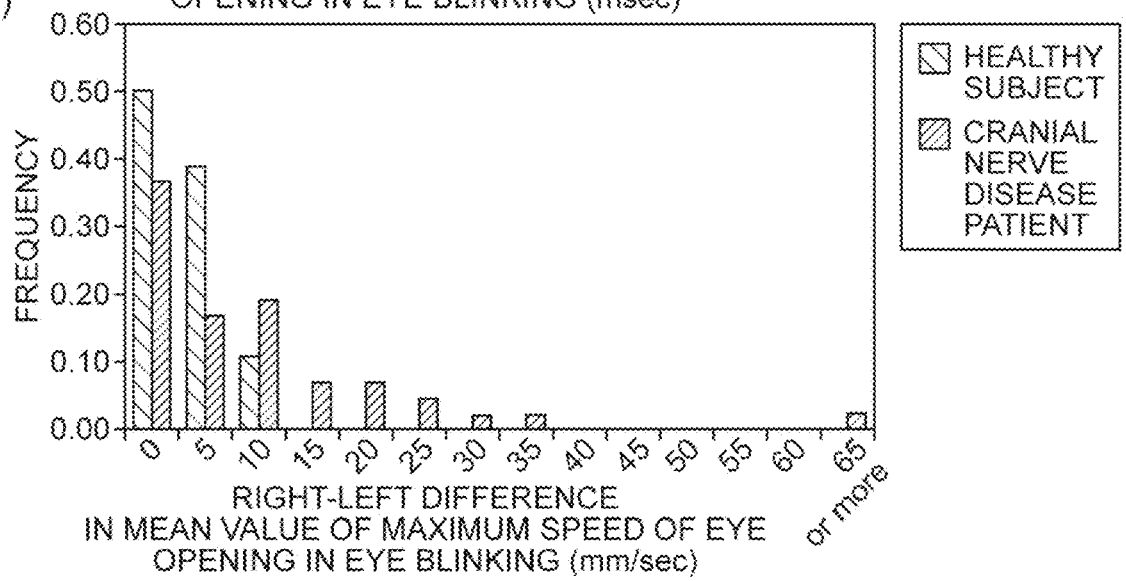

*Fig.23*
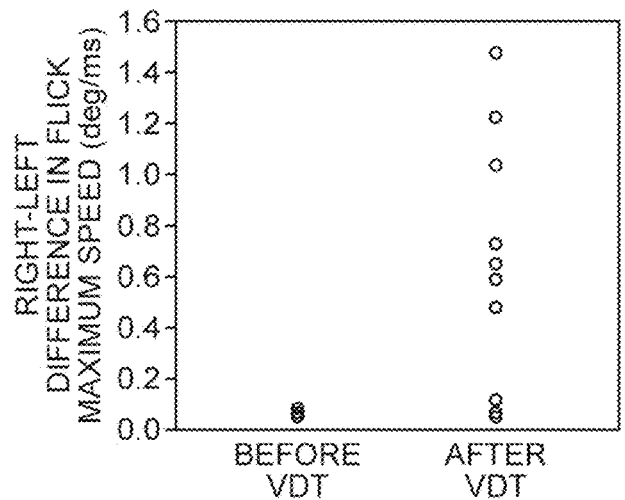
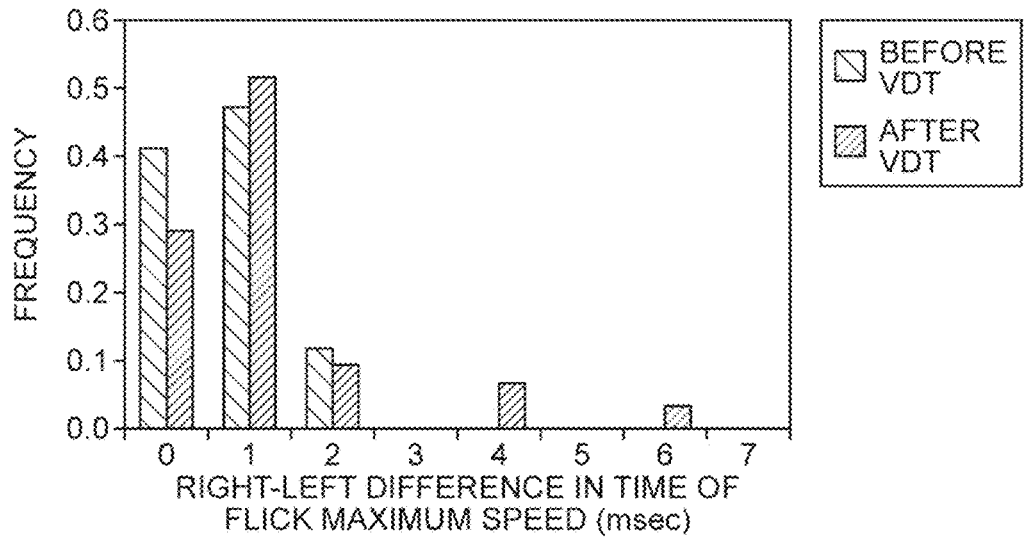
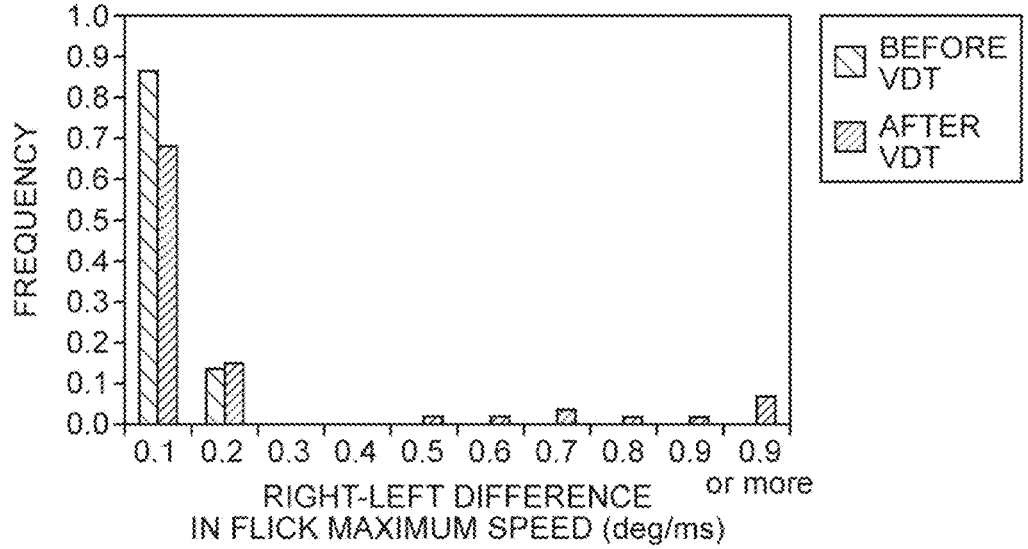

*Fig.25*
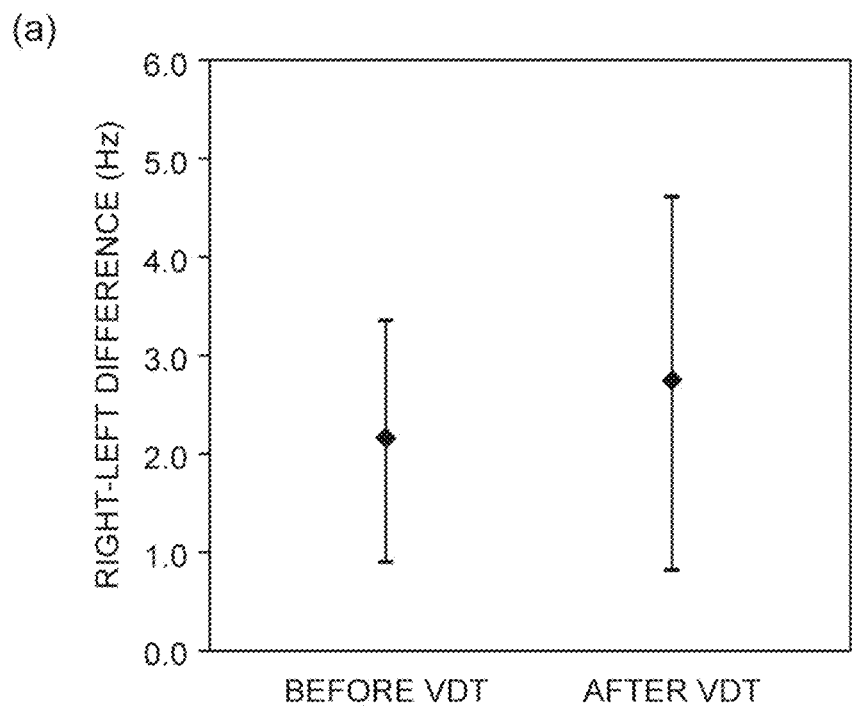
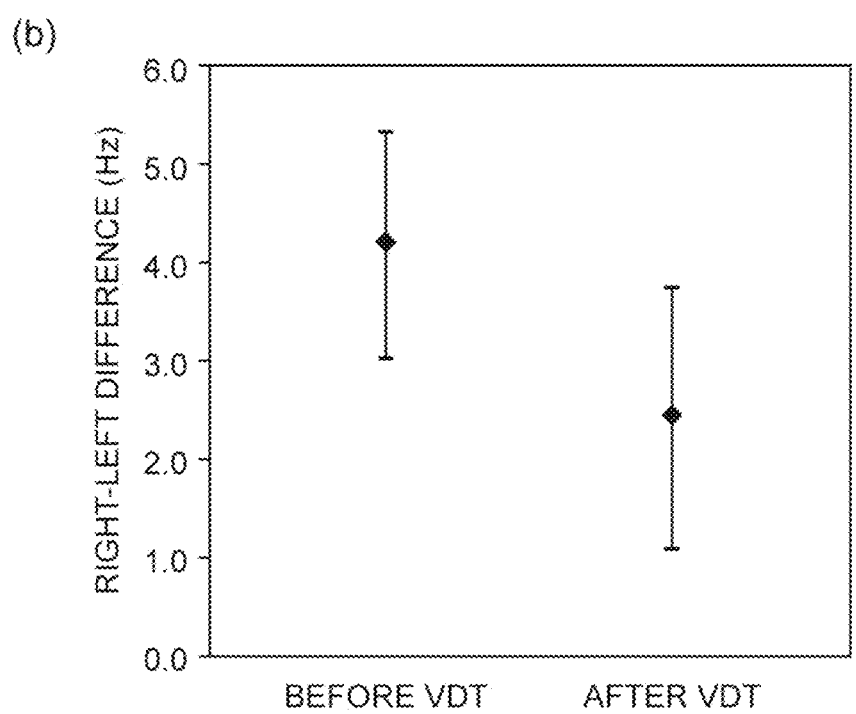

*Fig.26*
(a)
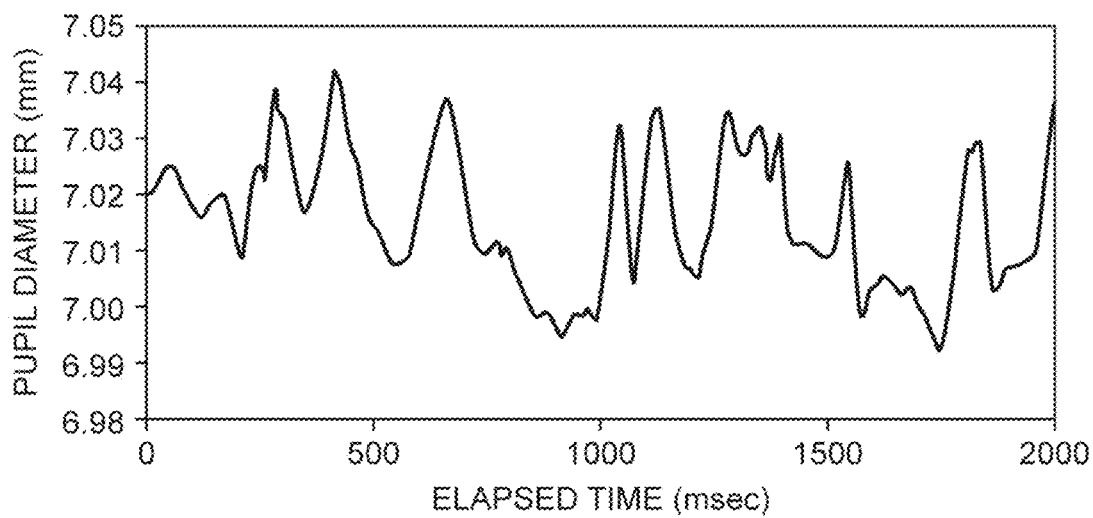
(b)
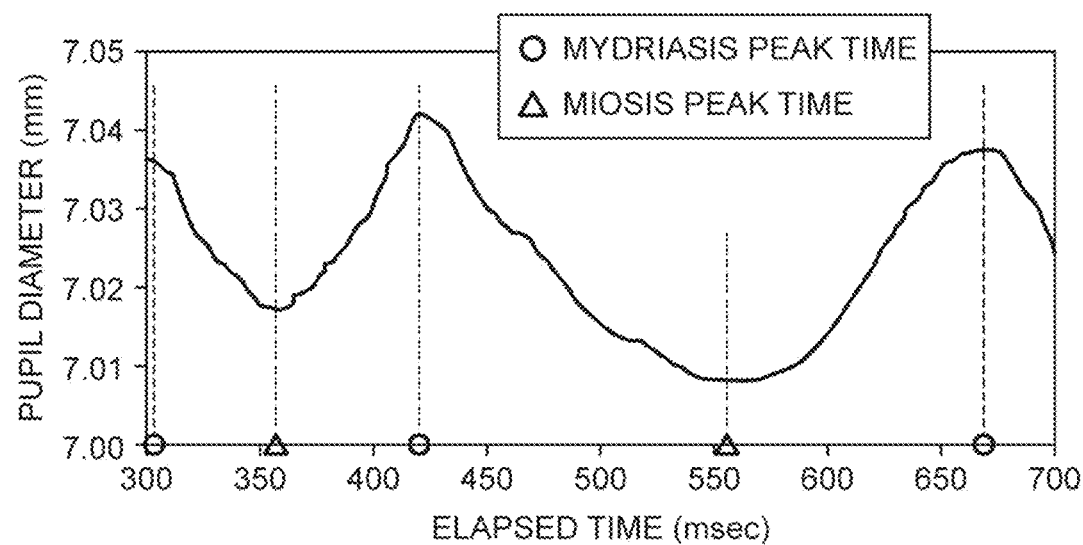

US 10,893,800 B2

BINOCULAR MEASUREMENT DEVICE, BINOCULAR MEASUREMENT METHOD, AND BINOCULAR MEASUREMENT PROGRAM

TECHNICAL FIELD

An aspect of the present invention relates to a binocular measurement device, a binocular measurement method, and a binocular measurement program to measure both eyes of a target person.

BACKGROUND ART

The eye is an organ differentiated from the brain in an organic process, and is only one organ capable of being observed non-invasively from the outside among organs directly linked to the brain. Therefore, it is considered that the health of the brain can be quantified by quantifying behavior of the eye area. Conventionally, for quantitative evaluation of brain functions, large-scale facilities such as PET (positron emission tomography), CT, and MRI are used. Such quantitative evaluation has achieved a measure of credibility. On the other hand, such quantitative evaluation has a problem in which the cost burden is high, and a doctor with specialized expertise for diagnosis is necessary. Therefore, it has been demanded to establish evaluation by a more convenient method.

On the other hand, conventionally, as one method of brain function measurement methods, a method for inspecting behavior of the eyes of a subject has been known. For example, a method for measuring eye blinking of a subject (refer to Non Patent Literature 1 listed below), and a method for measuring involuntary eye movement of a subject (refer to Non Patent Literature 2 listed below), etc., have been considered as one of the convenient methods for brain function disease extraction and screening.

CITATION LIST

Non Patent Literature

Non Patent Literature 1: Takahiro Niida, "Neuro-ophthalmology Introduction Series 96, Palpebra 2, Blinking," Neuro-ophthalmol. Jpn. Vol. 29 No. 2, pp. 204-212, 2012

Non Patent Literature 2: Engbert R., "Microsaccades: amicrocosm for research on oculomotor control, attention, and visual perception," Martinez-Conde, Macknik, Martinez, Alonso & Tse (Eds.), Progress in Brain Research, 2006, vol. 154, pp. 177-192

SUMMARY OF INVENTION

Technical Problem

However, with the method described in Non Patent Literature 1 listed above, a reflexive eyeblink caused by electrostimulation is measured by using an evoked potential recording device with a plurality of electrodes, and a burden on a subject at the time of an inspection tends to increase. In addition, by the methods described in Non Patent Literature 1 and Non Patent Literature 2, it is difficult to properly evaluate differences in behavior of both eyes of subjects.

Therefore, an aspect of the present invention was made in view of these problems, and an object thereof is to provide a binocular measurement device and a binocular measurement method capable of easily and properly evaluating differences in behavior of both eyes of subjects.

Solution to Problem

In order to solve the above-described problems, the inventors of the present invention examined a method of quantitative evaluation of differences in behavior of both eyes between patients suffering from various diseases such as Parkinson's disease and healthy people. As a result, the inventors of the present invention found that evaluation of a comparison value obtained by comparing a feature amount calculated based on movement of the right eye and a feature amount calculated based on movement of the left eye could be used as a new index for discrimination between a brain disease patient and a healthy person or for quantitative evaluation of states before and after a fatigue work.

That is, a binocular measurement device according to an embodiment of the present invention includes a photodetector that detects light from the right eye and the left eye of a target person, and outputs detection signal of the light, a feature amount calculating unit that calculates a first feature amount corresponding to the right eye and a second feature amount corresponding to the left eye based on the detection signal, and a comparison value calculating unit that calculates, based on the first feature amount and the second feature amount, a comparison value obtained by comparing the first feature amount and the second feature amount.

Alternatively, a binocular measurement method according to another embodiment of the present invention includes a step of detecting light from the right eye and the left eye of a target person by using a photodetector, and outputting a detection signal of the light, a step of calculating a first feature amount corresponding to the right eye and a second feature amount corresponding to the left eye based on the detection signal, and a step of calculating, based on the first feature amount and the second feature amount, a comparison value obtained by comparing the first feature amount and the second feature amount.

Alternatively, a binocular measurement program according to another embodiment of the present invention makes a processor included in a binocular measurement device that measures both eyes of a target person by using an image of a portion including the right eye and the left eye of the target person, function as a feature amount calculating unit that calculates a first feature amount corresponding to the right eye and a second feature amount corresponding to the left eye based on the image, and a comparison value calculating unit that calculates, based on the first feature amount and the second feature amount, a comparison value obtained by comparing the first feature amount and the second feature amount.

By the binocular measurement device, the binocular measurement method, or the binocular measurement program according to the embodiments described above, based on detection signal (image) of light from the right eye and the left eye, a first feature amount related to the right eye and a second feature amount related to the left eye are calculated, and a comparison value obtained by comparing the first feature amount and the second feature amount is calculated. Accordingly, an evaluation value related to behavior of the eyes of the target person can be acquired with a simple device configuration without a burden on the target person. Further, based on this evaluation value, behavior of the eyes of the target person can be properly evaluated.

Advantageous Effects of Invention

According to an aspect of the present invention, differences in behavior of both eyes of subjects can be easily and properly evaluated.

BRIEF DESCRIPTION OF DRAWINGS

FIG. 5 are graphs showing frequency values of right-left differences in time of maximum speed of eye closing in eye blinking and frequency values of right-left differences in maximum speed of eye closing in eye blinking obtained by the binocular measurement system 1 shown in FIG. 1.

FIG. 6 are graphs showing mean values of right-left differences in time of maximum speed of eye closing in eye blinking and variance values of right-left differences in time of maximum speed of eye closing in eye blinking.

FIG. 7 are graphs showing standard deviations of right-left differences in time of maximum speed of eye closing in eye blinking and differences between maximum values and minimum values of right-left differences in time of maximum speed of eye closing in eye blinking obtained by the binocular measurement system 1 shown in FIG. 1.

FIG. 8 are graphs showing maximum values of right-left differences in time of maximum speed of eye closing in eye blinking and minimum values of right-left differences in time of maximum speed of eye closing in eye blinking obtained by the binocular measurement system 1 shown in FIG. 1.

FIG. 9 are graphs showing mean values of right-left differences in maximum speed of eye closing in eye blinking and variance values of right-left differences in maximum speed of eye closing in eye blinking obtained by the binocular measurement system 1 shown in FIG. 1.

FIG. 10 are graphs showing standard deviations of right-left differences in maximum speed of eye closing in eye blinking and differences between maximum values and minimum values of right-left differences in maximum speed of eye closing in eye blinking obtained by the binocular measurement system 1 shown in FIG. 1.

FIG. 11 are graphs showing maximum values of right-left differences in maximum speed of eye closing in eye blinking and minimum values of right-left differences in maximum speed of eye closing in eye blinking obtained by the binocular measurement system 1 shown in FIG. 1.

FIG. 12 are graphs showing a distribution of mean values of maximum speeds of eye closing in eye blinking of the left eyes, a distribution of mean values of maximum speeds of eye closing in eye blinking of the right eyes, and a distribution of right-left differences in mean value of maximum speeds of eye closing in eye blinking obtained by the binocular measurement system 1 shown in FIG. 1.

FIG. 13 are graphs showing mean values and standard deviations of right-left differences in time of maximum speed of eye closing in eye blinking, and mean values and standard deviations of right-left differences in maximum speed of eye closing in eye blinking obtained by the binocular measurement system 1 shown in FIG. 1.

FIG. 15 are graphs showing frequencies of right-left differences in mean value of upper eyelid movement amounts at the time of eye opening in eye blinking, frequencies of right-left differences in mean value of periods of eye opening in eye blinking, and frequencies of right-left differences in mean value of maximum speeds of eye opening in eye blinking obtained by the binocular measurement system 1 shown in FIG. 1.

FIG. 23 are graphs showing right-left differences in flick maximum speed and right-left differences in time of flick maximum speed obtained by the binocular measurement system 1 shown in FIG. 1.

FIG. 25 are graphs showing mean values of right-left differences in movement frequency of tremor and standard deviations of the right-left differences obtained by the binocular measurement system 1 shown in FIG. 1.

FIG. 26 are graphs showing examples of temporal changes of pupil diameters calculated by the feature amount calculating unit 11 shown in FIG. 1.

DESCRIPTION OF EMBODIMENTS

Hereinafter, preferred embodiments of a binocular measurement device, a binocular measurement method, and a binocular measurement program according to the present invention will be described in detail with reference to the drawings. In addition, the same or corresponding parts will be denoted by the same reference signs in the description of the drawings, and overlapping description will be omitted.

Figure 1:
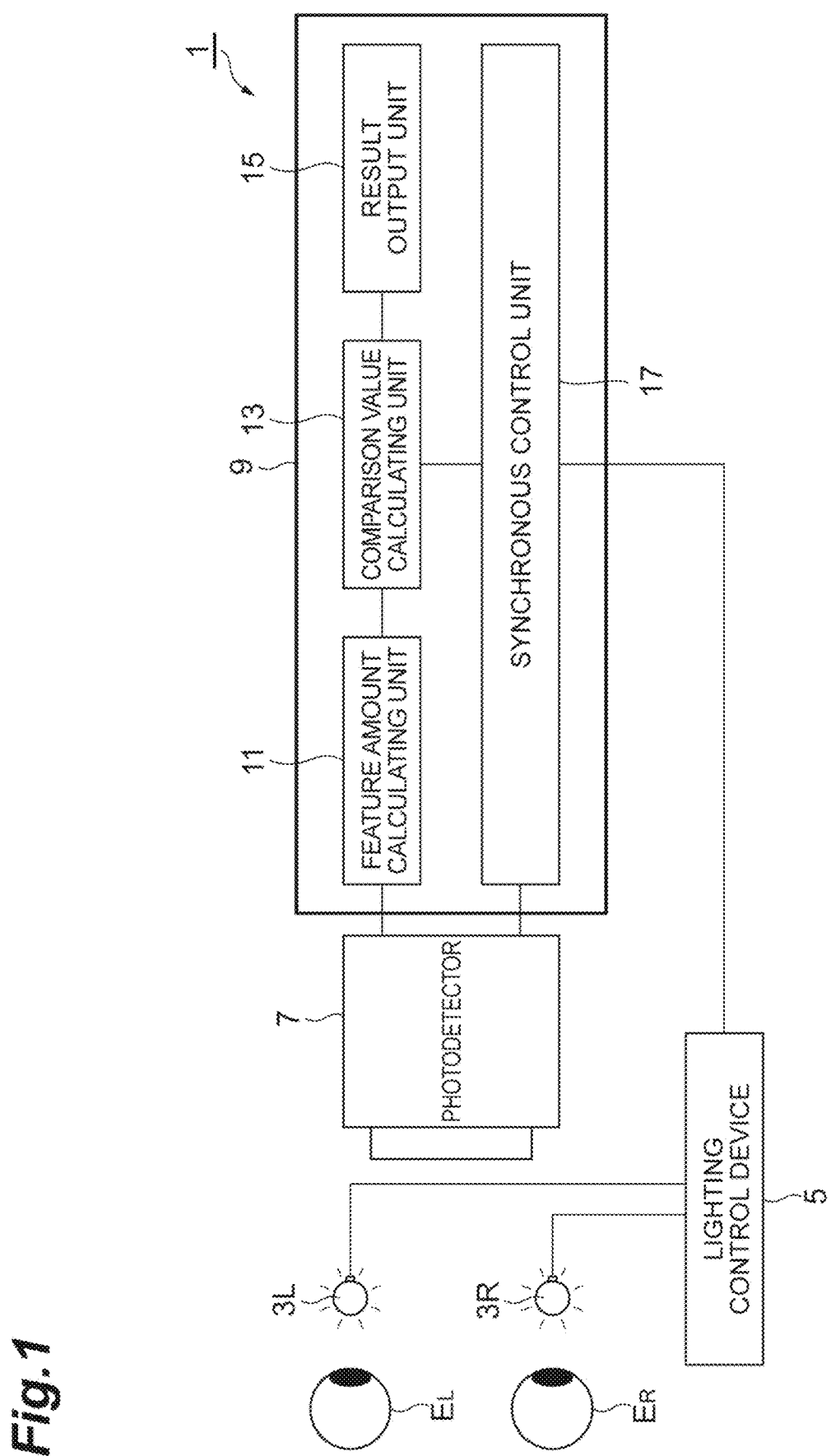
FIG. 1 is a block diagram showing a schematic configuration of a binocular measurement system 1 according to an embodiment of the present invention.

FIG. 1 is a block diagram showing a schematic configuration of a binocular measurement system 1 according to a preferred embodiment of the present invention. The binocular measurement system 1 shown in FIG. 1 is configured to temporally continuously detect light from the right eye $E_R$ and the left eye $E_L$ of a subject (target person) at a predetermined frame rate, and quantify and output differences in behavior between the right and left eyes of the subject. This binocular measurement system 1 includes light sources 3R and 3L that irradiate illumination light onto the right eye $E_R$ and the left eye $E_L$ of a target person, a lighting control device 5 that controls the light sources 3R and 3L, a photodetector 7 that detects light from the right eye $E_R$ and the left eye $E_L$, and a processor 9 that processes detection signal output from the photodetector 7.

The light sources 3R and 3L are illuminating means that illuminates the right eye $E_R$ and the left eye $E_L$ of a subject including their peripheries, and preferably consist of, for example, LEDs that generate infrared light. When the light sources 3R and 3L irradiate infrared light onto the eyes $E_R$ and $E_L$ and their peripheries, the infrared light is reflected on the eyes $E_R$ and $E_L$ and their peripheries and light images are generated. The light sources 3R and 3L are not limited to the infrared LEDs, and other kinds of light sources may be used. For example, light sources that generate near infrared light may be used, lamp light sources combined with films that transmit infrared light or near infrared light may be used, or laser beams satisfying safety standards may be used as direct light or indirect light. In addition, as a configuration to realize proper illuminance, in addition to a configuration using a plurality of illumination lamps, these light sources may have a configuration in which a lens is incorporated in a light emitting unit to suppress scattering of the illumination light and efficiently illuminate a desired region. In these light sources, a configuration that performs efficient eye area illumination by shaping energy of a laser beam into a desired lighting shape by using a spatial modulation device, may be adopted.

The lighting control device 5 is a control unit that controls light intensities of the light sources 3R and 3L so as to respectively illuminate the right eye $E_R$ and the left eye $E_L$ of a subject at predetermined brightness. In addition, the lighting control device 5 adjusts and controls light intensities and emission wavelengths of the light sources 3R and 3L so as to obtain light intensities, illumination light wavelengths, and reflected light shapes suitable for details of detection targeting the right eye $E_R$ and the left eye $E_L$ of a subject. Further, the lighting control device 5 is electrically connected to the processor 9, and according to synchronous control by the processor 9, controls light emission timings with respect to the right eye $E_R$ and the left eye $E_L$ of a subject. In order to enable the processor 9 or the photodetector 7 to determine whether the right eye $E_R$ and the left eye $E_L$ of a subject are within a measurement range of the photodetector 7, or in order to realize a function of positioning the right eye $E_R$ and the left eye $E_L$ of a subject by the processor 9 or the photodetector 7, the lighting control device 5 may control illumination light of the light sources 3R and 3L to flash before the start of measurement.

The photodetector 7 is an imaging device that has a light receiving surface with a plurality of pixels two-dimensionally arrayed, and detects reflected light from the right eye $E_R$ and the left eye $E_L$ at a predetermined frame rate and generates and outputs two-dimensional image signal (detection signal). As such an imaging device, a vision camera having a vision chip that performs processing from image acquisition to image processing can be used. As this photodetector 7, two photodetectors may individually and respectively capture the right eye $E_R$ and the left eye $E_L$ of a subject, or one photodetector may simultaneously capture the right eye $E_R$ and the left eye $E_L$ of a subject. The photodetector 7 may be combined with a plurality of imaging devices that have specifications or settings (for example, wavelength sensitivity, light intensity sensitivity, angle of view of lens, magnification of lens, and frame rate, etc.) respectively optimal for eyeball movement, involuntary eye movement, eye blinking, and pupils to be detected of a subject.

The photodetector 7 is preferably configured to be capable of performing capturing at a frame rate higher than that of a general video camera, and is preferably set to have a frame rate of a frequency twice or more as high as a movement frequency to be detected of a subject. For example, when tremor of involuntary eye movement is to be detected, tremor is movement of approximately 100 Hz, so that a photodetector 7 with a frame rate of 200 Hz or more is used. When microsaccade is to be detected, microsaccade takes approximately 20 msec in many cases, so that a photodetector 7 with a frame rate of 100 Hz or more is used. An eyelid movement at the time of eye blinking takes approximately 200 msec, so that when the frame rate is approximately 10 Hz, rough eyelid motion behavior can be detected. However, in order to enable detection of fine irregular movement at the time of eye blinking, not only a high frame rate but also high accuracy are required for the measurement. Therefore, when eyelid movement at the time of eye blinking is to be detected, a photodetector 7 configured not only to have a high frame rate but also to be capable of imaging at high resolution is used.

Here, a photodetector 7 other than a video camera may be used. In a case where eyeball movement and involuntary eye movement are to be detected and a video camera is used as the photodetector 7, cornea reflected light is detected from image signals, and by gravity center arithmetic operation, temporal changes of eyeball positions are obtained. Instead, as the photodetector 7, in addition to a sensor such as a profile sensor that detects a position of a bright spot and outputs positional information, a simpler sensor such as a photodiode, a photodetector, a linear sensor, or an area sensor may be used. In a case where eye blinking is to be detected and a video camera is used as the photodetector 7, eyelid position extraction processing using image processing technologies such as edge extraction and Hough transform, or processing to obtain an eyelid position from a luminance profile calculated from an image signal, is performed. Instead, as the photodetector 7, a configuration including a lighting unit (for example, a line laser, an LED array, etc.) that irradiates and projects a marker having a linear shape or the like on an eye area, and a detection unit (for example, a profile sensor, a photodiode, a photodetector, a linear sensor, an area sensor, etc.) that extracts an eyelid position by capturing reflection on an eye surface without capturing scattered light on the skin, may be adopted. In a case where the pupils are to be detected and a video camera is used as the photodetector 7, by extracting a portion made bright by reflected light generated when irradiating illumination light onto the pupil from the front side by binarization of image processing, a pupillary area is extracted. Instead, it is also allowed that information on a temporal change of a pupillary area is acquired by detecting a sum of brightness values of the portion made bright by using a photodiode or a photodetector. The sum of brightness values detected herein bears a proportionate relationship to the pupillary area.

The processor 9 is an image processing circuit, and processes image signals output from the photodetector 7. The processor 9 is constituted by a personal computer with a CPU and a memory such as a RAM or a ROM incorporated inside, or a mobile terminal, etc., typified by a smartphone or a tablet computer. The processor 9 may also be constituted by an FPGA (field programmable gate array). This processor 9 includes, as functional constituent elements, a feature amount calculating unit 11, a comparison value calculating unit 13, a result output unit 15, and a synchronous control unit 17. The feature amount calculating unit 11, comparison value calculating unit 13, result output unit 15, and synchronous control unit 17 may be realized by hardware inside the processor 9, or may be realized by software (a binocular measurement program) stored in the processor 9. Functions of the feature amount calculating unit 11, the comparison value calculating unit 13, the result output unit 15, and the synchronous control unit 17 may be realized by the same processor, or may be realized by different processors. A program to make the processor 9 function as the feature amount calculating unit 11, the comparison value calculating unit 13, the result output unit 15, and the synchronous control unit 17 may be stored in a storage device (storage medium) inside the processor 9, or may be stored in a storage medium electrically connected to the processor 9.

The feature amount calculating unit 11 of the processor 9 calculates a right eye feature amount corresponding to the right eye $E_R$ of a subject and a left eye feature amount corresponding to the left eye $E_L$ of the subject based on image signal output from the photodetector 7. For example, as a right eye feature amount and a left eye feature amount, the feature amount calculating unit 11 calculates a feature amount related to eye blinking, a feature amount related to involuntary eye movement, and a feature amount related to the pupil. At this time, the feature amount calculating unit 11 may calculate all of these three kinds of feature amounts, or may calculate a part of them. The involuntary eye movement to be calculated as a feature amount includes tremor being fine movement with an amplitude of approximately 1 μm (20 to 40 arcseconds) and a frequency of about 100 Hz, drift being slow displacing movement, and flick (also referred to as microsaccade) being saccadic eye movement (saltation movement) of 0.04 degree angle to 2 minutes of arc occurring after drift.

Based on the right eye feature amount and the left eye feature amount calculated by the feature amount calculating unit 11, the comparison value calculating unit 13 of the processor 9 calculates a comparison value obtained by comparing a right eye feature amount and a left eye feature amount. The comparison value calculating unit 13 may directly calculate a comparison value from the right eye feature amount and the left eye feature amount, or may calculate statistics from the respective right eye feature amount and left eye feature amount, and calculate a comparison value of these statistics. Such statistics are statistics obtained from high-order moments such as a mean, a variance, a standard deviation, kurtosis, and skewness, a median value, a quartile point, a maximum value, a minimum value, a mode value, and a difference between the maximum value and the minimum value, etc. At this time, the comparison value calculating unit 13 calculates, as a comparison value, an absolute value of a difference between the right eye feature amount and the left eye feature amount, or a ratio between the right eye feature amount and the left eye feature amount.

The result output unit 15 of the processor 9 outputs a comparison value calculated by the comparison value calculating unit 13 to an output device such as a display. At this time, the result output unit 15 may output a comparison value to the outside by using wireless communications, wired communications, or the like, or output a comparison value to the memory inside. The result output unit 15 may output, in addition to numerical data represented by a comparison value, text data and acquired images as they are, or may output statistics of numerical data showing comparison values. Such statistics are statistics obtained from high-order moments such as a mean, a variance, a standard deviation, kurtosis, and skewness, a median value, a quartile point, a maximum value, a minimum value, a mode value, and a difference between the maximum value and the minimum value, etc. The result output unit 15 may output an aggregated value such as a mean value obtained by aggregating comparison values, or may set a threshold and output a period during which a comparison value exceeds the threshold, or similar data, and frequency, etc.

The synchronous control unit 17 of the processor 9 controls synchronization of operations of the respective devices and the respective function units in the binocular measurement system 1. For example, the synchronous control unit 17 controls synchronization between a timing of capturing (detection) by the photodetector 7 and emission timings of the light sources 3R and 3L. The synchronous control unit 17 controls operation timings of the feature amount calculating unit 11, the comparison value calculating unit 13, and the result output unit 15 according to output timings of image signals by the photodetector 7. For the processor 9, a configuration that makes the respective devices and the respective function units operate asynchronously by using a shared memory instead of the synchronous control unit 17 may be adopted. For example, the photodetector 7 occasionally saves image data based on image signal in a shared memory, and the feature amount calculating unit 11 occasionally monitors whether image data has been newly saved in the shared memory, and calculates a right eye feature amount and a left eye feature amount at a timing at which saving is detected, and saves these in the shared memory. At the same time, the comparison value calculating unit 13 occasionally monitors whether a right eye feature amount and a left eye feature amount have been newly saved in the shared memory, and at a timing at which saving of new right eye feature amount and left eye feature amount is detected, calculates a comparison value based on these amounts as targets and saves the comparison value in the shared memory. Similarly, the result output unit 15 always monitors whether a comparison value has been saved in the shared memory, and at a timing at which saving of a new comparison value is detected, outputs the comparison value and data related to the comparison value. The result output unit 15 may output a comparison value at a timing at which it receives signals of ends of processing from the photodetector 7, the feature amount calculating unit 11, and the comparison value calculating unit 13. In this case, control of the lighting control device 5 may be performed from the photodetector 7, or may be performed from the feature amount calculating unit 11 or the comparison value calculating unit 13 inside the processor 9.

Here, the lighting control device 5 described above may be incorporated in the photodetector 7 or the processor 9. For example, when a vision camera having an arithmetic operation function is used as the photodetector 7, the photodetector 7 has a function to output processing results and external control signals, etc., in addition to an image processing function. By using this photodetector 7, real-time control such as flashing control, etc., of the light sources 3R and 3L may be performed in parallel with image processing.

Similarly, a part or all of the function units of the processor 9 may be incorporated in the photodetector 7. For example, a pattern in which the photodetector 7 performs processing up to output of image signals and subsequent processing is performed by the processor 9 may be adopted, a pattern in which a part of processing of the feature amount calculating unit 11 is performed by the photodetector 7 and subsequent processing is performed by the processor 9 may be adopted, or a pattern in which processing up to feature amount calculation processing of the feature amount calculating unit 11 is performed by the photodetector 7 and subsequent processing is performed by the processor 9 may be adopted.

The photodetector 7 or the processor 9 may have a function to determine whether the right eye $E_R$ and the left eye $E_L$ of a subject are within a measurement range of the photodetector 7. In detail, the processor 9 performs control to make the light sources 3R and 3L flash with a predetermined period by the lighting control device 5 before the start of measurement, and simultaneously, by determining whether a portion that flashes with a predetermined period and at a predetermined luminance is present in an image signal acquired by the photodetector 7, and deter mines whether an eye area is present within the measurement range. This utilizes a fact that illumination light scatters on the skin and hair and is reflected on an eye area, and as a result, an eye area is caught brightly in an image signal. By controlling the two light sources 3R and 3L so as to flash at different periods, the processor 9 can grasp the positions of the right eye $E_R$ and the left eye $E_L$. Since positions of both eyes $E_R$ and $E_L$ can be grasped, in the case where a video camera is used as the photodetector 7, by partially reading only a portion corresponding to an eye area in an image signal, it becomes possible to set a frame rate for measurement to be higher, and reduce a file size of a data region to be used to save image data.

Hereinafter, the function of the processor 9 to calculate feature amounts and comparison values will be described in detail. The processor 9 of the present embodiment is set to detect eye blinking of a subject.

Figure 2:
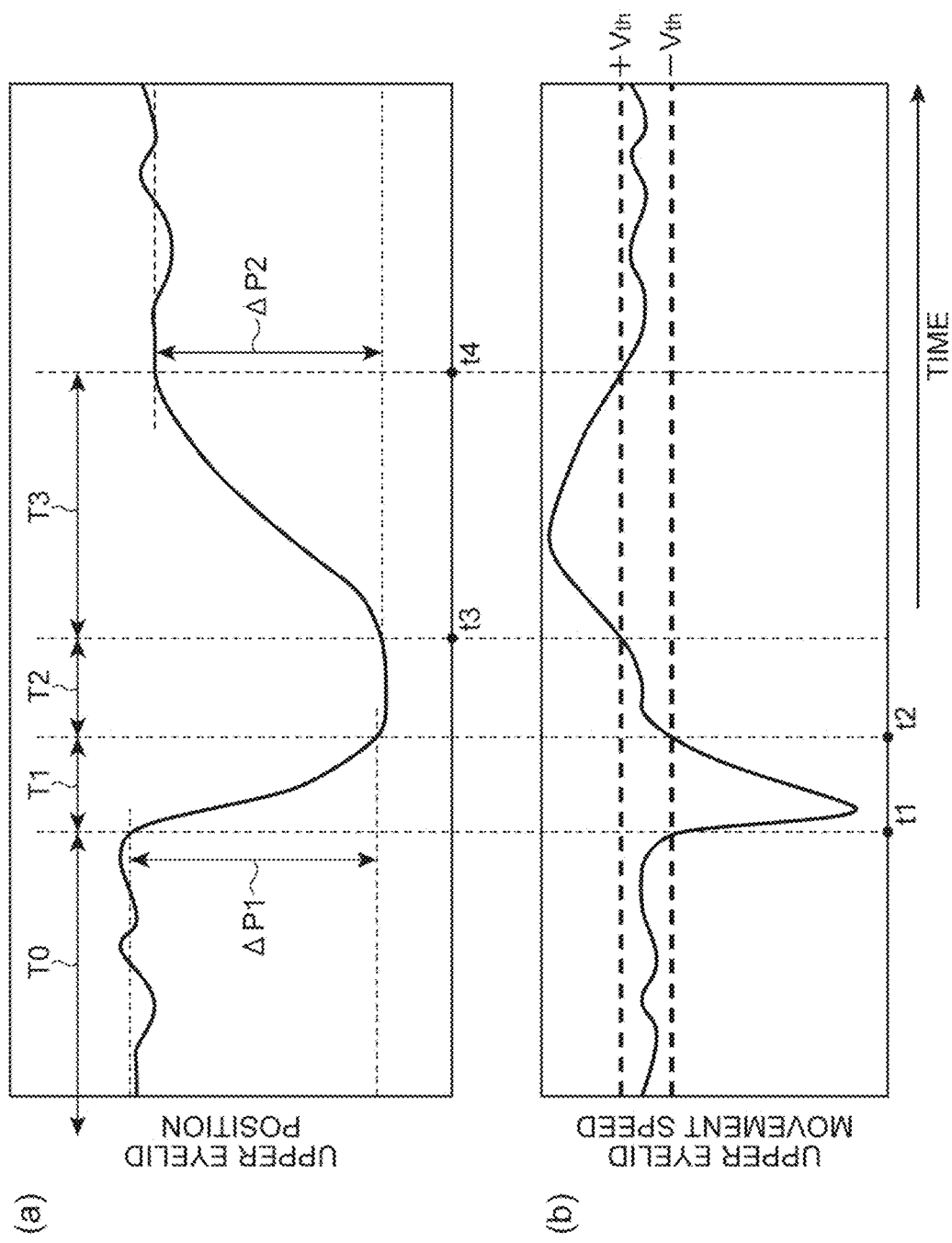
FIG. 2 are graphs showing temporal changes of an upper eyelid position and an upper eyelid movement speed calculated by a feature amount calculating unit 11 shown in FIG. 1.

The feature amount calculating unit 11 of the processor 9 calculates a temporal change of an upper eyelid position based on an image signal output from the photodetector 7. The upper eyelid position is calculated by applying image processing such as edge extraction and Hough transform targeting the image signal, or processing to obtain an eyelid position from a luminance profile calculated from the image signal (refer to Japanese Unexamined Patent Publication No. 2012-085691). In addition, the feature amount calculating unit 11 calculates a temporal change of an upper eyelid movement speed based on the temporal change of the upper eyelid position. A portion (a) of FIG. 2 is a graph showing an example of a temporal change of an upper eyelid position calculated by the feature amount calculating unit 11, and a portion (b) of FIG. 2 is a graph showing an example of a temporal change of an upper eyelid movement speed calculated by the feature amount calculating unit 11. ±Vth shown in the portion (b) of FIG. 2 shows an eyeblink motion detection threshold. A period in which the upper eyelid moves at a speed higher than this threshold is defined as an eye blinking period, and as shown in the portion (a) of FIG. 2, lowering and rising of the upper eyelid position according to eyeblink motion of the subject are detected, and as shown in the portion (b) of FIG. 2, a peak of the speed during lowering of the upper eyelid position and a peak of the speed during rising of the upper eyelid position are detected. Thus, a state where the upper eyelid positioned at the upper side in an eye opening state lowers according to eye blinking, and when it fully lowers, an eye closure state is maintained for a while, and then, the eye is gradually opened is shown. A state where the upper eyelid movement speed changes to decrease at the time of eye closure, and the upper eyelid movement speed changes to increase at the time of eye opening, is shown. The feature amount calculating unit 11 calculates the temporal change of the upper eyelid position and the temporal change of the upper eyelid movement speed for each of the right eye $E_R$ and the left eye $E_L$, separately.

Further, the feature amount calculating unit 11 calculates an eyeblink feature amount being a feature amount related to eye blinking for each of the right eye $E_R$ and the left eye $E_L$, separately, based on the calculated temporal change of the upper eyelid position and the calculated temporal change of the upper eyelid movement speed. First, by comparing the temporal change of the upper eyelid movement speed with a negative speed threshold $-V_{th}$ set in advance, the feature amount calculating unit 11 identifies a time the upper eyelid movement speed exceeds the speed threshold $-V_{th}$ from the start of eye blinking as a start time t1 of a period T1 of eye closing in eye blinking, and identifies a time the upper eyelid movement speed starts to fall below the speed threshold $-V_{th}$ again after the time t1 as an ending time t2 of the period T1 of eye closing in eye blinking and as a start time t2 of an eye closure period T2. Further, the feature amount calculating unit 11 identifies, in the temporal change of the upper eyelid movement speed, a time the upper eyelid movement speed starts to surpass the positive speed threshold $+V_{th}$ set in advance after the time t2 as an ending time t3 of the eye closure period T2, and as a start time t3 of a period T3 of eye opening in eye blinking, and identifies a time the upper eyelid movement speed starts to fall below the speed threshold $+V_{th}$ again after the time t3 as an ending time t4 of the period T3 of eye opening in eye blinking. Then, the feature amount calculating unit 11 calculates, as an eyeblink feature amount, at least one of a "time interval from previous eye blinking," an "upper eyelid movement amount during eye closing in eye blinking," a "period of eye closing in eye blinking," a "maximum speed of eye closing in eye blinking," a "time of maximum speed of eye closing in eye blinking," an "eye closure period," an "upper eyelid movement amount during eye opening in eye blinking," a "period of eye opening in eye blinking," a "maximum speed of eye opening in eye blinking," and a "time of a maximum speed of eye opening in eye blinking." The "time interval from the previous eye blinking" is calculated as a period T0 between the start time t1 detected at the time of the previous eyeblink motion and the start time t1 detected at this time. The "upper eyelid movement amount during eye closing in eye blinking" is calculated as a movement amount ΔP1 of the upper eyelid during the period T1 of eye closing in eye blinking, the "period of eye closing in eye blinking" is calculated as a length of the period T1, the "maximum speed of eye closing in eye blinking" is calculated as a maximum speed in the period T1, the "time of the maximum speed of eye closing in eye blinking" is calculated as a time the speed is detected, and the "eye closure period" is calculated as a length of the period T2. Further, the "upper eyelid movement amount during eye opening in eye blinking" is calculated as a movement amount ΔP2 of the upper eyelid in the period T3 of eye opening in eye blinking, the "period of eye opening in eye blinking" is calculated as a length of the period T3, the "maximum speed of eye opening in eye blinking" is calculated as a maximum speed in the period T3, and the "time of maximum speed of eye opening in eye blinking" is calculated as a time the speed is detected.

The comparison value calculating unit 13 of the processor 9 calculates a comparison value by using the eyeblink feature amounts of the respective right eye $E_R$ and left eye $E_L$ calculated by the feature amount calculating unit 11. The comparison value calculating unit 13 may directly calculate a comparison value from the two eyeblink feature amounts, or may calculate statistics from the two eyeblink feature amounts, and calculate a comparison value of the statistics. In the case of calculation of statistics, for each of the right eye $E_R$ and the left eye $E_L$, the comparison value calculating unit 13 calculates statistics such as a mean value based on a plurality of feature amounts temporally continuously obtained during measurement as targets.

In addition, the result output unit 15 of the processor 9 outputs numerical data, text data, or acquired images based on the comparison value calculated by the comparison value calculating unit 13. Here, the result output unit 15 may output data showing the comparison value itself, or may output statistics of numerical data showing the comparison value. In this case, the result output unit 15 calculates statistics such as a mean value based on a plurality of comparison values temporally continuously obtained during measurement as targets.

Figure 3:
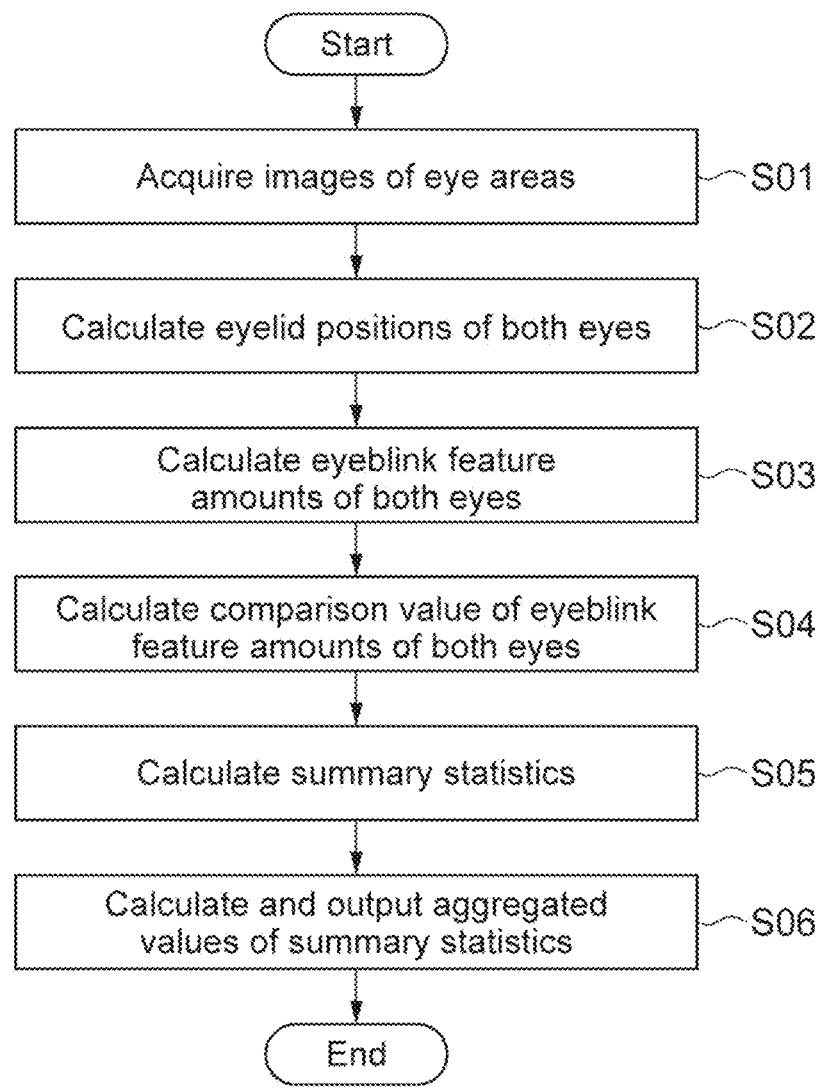
FIG. 3 is a flowchart showing steps of a comparison value measurement operation by the binocular measurement system 1 shown in FIG. 1.
Figure 4:
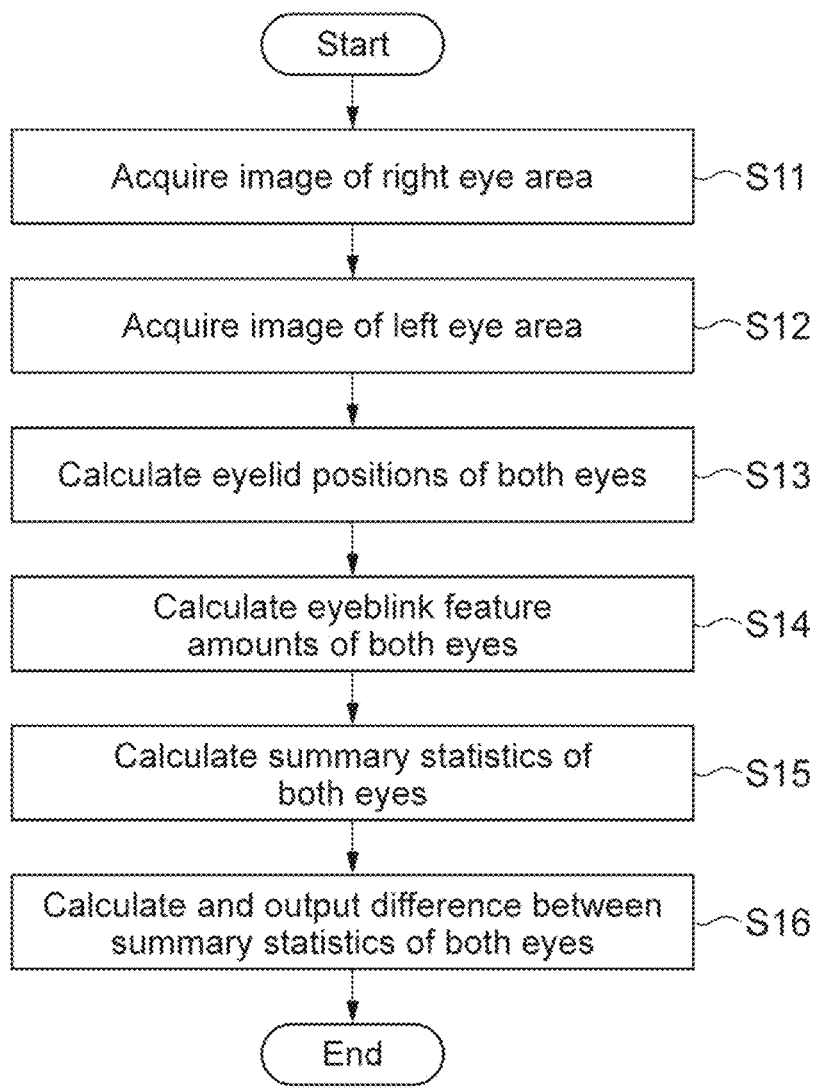
FIG. 4 is a flowchart showing steps of a comparison value measurement operation by the binocular measurement system 1 shown in FIG. 1.

Next, detailed steps of a comparison value measurement operation by the binocular measurement system 1 will be described, and a binocular measurement method according to the present embodiment will be described in detail. FIG. 3 and FIG. 4 are flowcharts showing steps of a comparison value measurement operation by the binocular measurement system 1. FIG. 3 shows steps in a case where statistics are calculated based on, as a target, a comparison value of eyeblink feature amounts by simultaneously acquiring images of the right eye $E_R$ and the left eye $E_L$, and FIG. 4 shows steps in a case where images of the right eye $E_R$ and the left eye $E_L$ are acquired separately, an eyeblink feature amount and a statistic thereof are calculated for each of the right eye $E_R$ and the left eye $E_L$ separately, and a comparison value of the two statistics is calculated. Either one of the functions only needs to be implemented in the binocular measurement system 1.

First, referring to FIG. 3, when a measurement operation is started, image signals of the right eye $E_R$ and the left eye $E_L$ are temporally continuously and simultaneously acquired by the photodetector 7 (Step S01). Next, by the feature amount calculating unit 11, temporal changes of the upper eyelid positions of the right eye $E_R$ and the left eye $E_L$ of the subject are calculated based on the image signals (Step S02). Then, by the feature amount calculating unit 11, based on the temporal changes of the upper eyelid positions of the right eye $E_R$ and the left eye $E_L$, eyeblink feature amounts of the respective right eye $E_R$ and left eye $E_L$ are temporally continuously calculated (Step S03). Thereafter, by the comparison value calculating unit 13, a comparison value of the eyeblink feature amounts of the respective right eye $E_R$ and left eye $E_L$ is temporally continuously calculated (Step S04). Next, by the result output unit 15, statistics of the comparison value temporally continuously obtained are calculated (Step S05). Then, aggregated values of these statistics are calculated and output (Step S06). In these Steps S05 and S06, aggregated values of the comparison value may be directly output without calculation of statistics of the comparison value.

Referring to FIG. 4, when a measurement operation is started, image signals of the right eye $E_R$ and the left eye $E_L$ are temporally continuously and separately acquired by the photodetector 7 (Steps S11 and S12). Next, by the feature amount calculating unit 11, temporal changes of the upper eyelid positions of the right eye $E_R$ and the left eye $E_L$ of the subject are separately calculated based on the image signals (Step S13). Then, by the feature amount calculating unit 11, based on the temporal changes of the upper eyelid positions of the right eye $E_R$ and the left eye $E_L$, eyeblink feature amounts of the right eye $E_R$ and the left eye $E_L$ are temporally continuously calculated (Step S14). Thereafter, by the comparison value calculating unit 13, statistics of the eyeblink feature amounts of the respective right eye $E_R$ and left eye $E_L$ are separately calculated (Step S15). Next, by the comparison value calculating unit 13, comparison values of the statistics of the right eye $E_R$ and the left eye $E_L$ are calculated, and by the result output unit 15, these comparison values are output (Step S16). In these Steps S11 to S15, steps in which image signals of the right eye $E_R$ and the left eye $E_L$ are accumulated and then the collective calculation is performed are adopted, however, it is also allowed that after image acquisition and calculation processing for the right eye $E_R$ are performed, image acquisition and calculation processing for the left eye $E_L$ are performed.

According to the binocular measurement system 1 described above, based on image signals of reflected light from the right eye $E_R$ and the left eye $E_L$, an eyeblink feature amount related to the right eye $E_R$ and an eyeblink feature amount related to the left eye $E_L$ are calculated, and a comparison value is calculated by comparing the two eyeblink feature amounts. Accordingly, an evaluation value related to behavior of the eyes of the subject can be acquired by simple calculation processing using a simple device configuration without a burden on the subject. Further, based on this evaluation value, behavior of the eyes of the subject can be properly evaluated. In detail, brain functions can be non-invasively and easily quantified from behavior of the eyes.

Further, by using image signals obtained by an imaging device that generates a two-dimensional image as a detection target, feature amounts of the right eye $E_R$ and the left eye $E_L$ can be accurately obtained, and as a result, eye behavior evaluation accuracy can be improved.

Next, examples of measurement data obtained by the binocular measurement system 1 according to the present embodiment are shown.

A portion (a) of FIG. 5 shows frequency values of right-left differences in time of maximum speed of eye closing in eye blinking of one subject before and after performing a VDT work for 1 hour, and a portion (b) of FIG. 5 shows frequency values of right-left differences of maximum speed of eye closing in eye blinking of one subject before and after performing a VDT work for 1 hour. Here, a right-left difference is a value obtained by subtracting a value of the left eye from a value of the right eye, and a right-left difference being a positive value means that the value of the right eye is larger than the value of the left eye. The results shown in the portion (a) of FIG. 5 show that a right-left difference in time of maximum speed of eye closing in eye blinking becomes larger after the VDT work than before the VDT work, and the left eye reaches the maximum speed earlier than the right eye after the VDT work. The results shown in the portion (b) of FIG. 5 also show a similar tendency. That is, a right-left difference in maximum speed of eye closing in eye blinking becomes larger after the VDT work than before the VDT work, and the speed of the right eye was higher before the VDT work, and on the other hand, eye blinking in which the speed of the left eye is higher frequently occurs after the VDT work. In the binocular measurement system 1, a healthy people database and a disease database are provided, and by calculating Mahalanobis' generalized distances between these databases and the measurement data, the distances can be used as new feature amounts to quantify the functions of the eyes when judging which of a healthy people group and a disease group the measurement data is close to.

A portion (a) of FIG. 6 shows mean values of right-left differences in time of maximum speed of eye closing in eye blinking of three subjects before and after a VDT work, and a portion (b) of FIG. 6 shows variance values of right-left differences in time of maximum speed of eye closing in eye blinking of three subjects before and after a VDT work. The portion (a) of FIG. 6 shows that, after the VDT work, the right-left difference in time of maximum speed of eye closing in eye blinking tends to increase after the VDT work in any of the three subjects. The portion (b) of FIG. 6 shows that variation in the right-left difference in time of maximum speed of eye closing in eye blinking tends to increase after the VDT work in any of the three subjects.

A portion (a) of FIG. 7 shows standard deviations of right-left differences in time of maximum speed of eye closing in eye blinking of three subjects before and after a VDT work, and a portion (b) of FIG. 7 shows differences between maximum values and minimum values of right-left differences in time of maximum speed of eye closing in eye blinking of three subjects before and after a VDT work. The portion (a) of FIG. 7 shows that variation in the right-left difference in time of maximum speed of eye closing in eye blinking tends to increase after the VDT work in any of the three subjects. The portion (b) of FIG. 7 shows that variation in the right-left difference in time of maximum speed of eye closing in eye blinking tends to increase after the VDT work in any of the three subjects.

A portion (a) of FIG. 8 shows maximum values of right-left differences in time of maximum speed of eye closing in eye blinking of three subjects before and after a VDT work, and a portion (b) of FIG. 8 shows minimum values of right-left differences in time of maximum speed of eye closing in eye blinking of three subjects before and after a VDT work. The portion (a) of FIG. 8 shows that the right-left difference in time of maximum speed of eye closing in eye blinking tends to increase after the VDT work in any of the three subjects. The portion (b) of FIG. 8 shows that eye blinking in which the right-left difference in time of maximum speed of eye closing in eye blinking becomes shorter (the right-left difference becomes zero in some cases) occurs after the VDT work in any of the three subjects.

A portion (a) of FIG. 9 shows mean values of right-left differences in maximum speed of eye closing in eye blinking of three subjects before and after a VDT work, and a portion (b) of FIG. 9 shows variance values of right-left differences in maximum speed of eye closing in eye blinking of three subjects before and after a VDT work. The portion (a) of FIG. 9 shows that, after the VDT work, the right-left difference in maximum speed of eye closing in eye blinking tends to increase in any of the three subjects. The portion (b) of FIG. 9 shows that, after the VDT work, variation in the right-left difference in maximum speed of eye closing in eye blinking tends to increase in any of the three subjects.

A portion (a) of FIG. 10 shows standard deviations of right-left differences in maximum speed of eye closing in eye blinking of three subjects before and after a VDT work, and a portion (b) of FIG. 10 shows differences between maximum values and minimum values of right-left differences in maximum speed of eye closing in eye blinking of three subjects before and after a VDT work. The portion (a) of FIG. 10 shows that variation in the right-left difference in maximum speed of eye closing in eye blinking tends to increase after the VDT work in any of the three subjects. The portion (b) of FIG. 10 shows that variation in the right-left difference in maximum speed of eye closing in eye blinking tends to increase after the VDT work in any of the three subjects.

A portion (a) of FIG. 11 shows maximum values of right-left differences in maximum speed of eye closing in eye blinking of three subjects before and after a VDT work, and a portion (b) of FIG. 11 shows minimum values of right-left differences in maximum speed of eye closing in eye blinking of three subjects before and after a VDT work. The portion (a) of FIG. 11 shows that, after the VDT work, the right-left difference in maximum speed of eye closing in eye blinking tends to increase in any of the three subjects. The portion (b) of FIG. 11 shows that, after the VDT work, the right-left difference in maximum speed of eye closing in eye blinking tends to increase in any of the three subjects.

FIG. 12 show examples in which, targeting a plurality of subjects including healthy people and cranial nerve disease patients, statistics of eyeblink feature amounts are calculated for each of the right and left eyes, and then comparison values of the statistics are calculated. A portion (a) of FIG. 12 shows a distribution of mean values of maximum speeds of eye closing in eye blinking of the left eyes, a portion (b) of FIG. 12 shows a distribution of mean values of maximum speeds of eye closing in eye blinking of the right eyes, and a portion (c) of FIG. 12 shows a distribution of right-left differences in mean value of maximum speed of eye closing in eye blinking. From these results, it is found that the right-left difference in mean value of maximum speed of eye closing in eye blinking of a cranial nerve disease patient tends to be larger as compared with a healthy person.

A portion (a) of FIG. 13 shows mean values and standard deviations of right-left differences in time of maximum speed of eye closing in eye blinking of three subjects before and after a VDT work, and a portion (b) of FIG. 13 shows mean values and standard deviations of right-left differences in maximum speed of eye closing in eye blinking of three subjects before and after a VDT work. In each graph, a mean value is shown by a circle, and a standard deviation is shown by a bar length. As shown in the portion (a) of FIG. 13, it was found that the difference in time became larger and variation in the difference in time became larger after the VDT work than before the VDT work in any of the three subjects. Also, as shown in the portion (b) of FIG. 13, it was found that the speed difference became larger and the variation in the speed difference became larger after the VDT work than before the VDT work in any of the three subjects.

Figure 14:
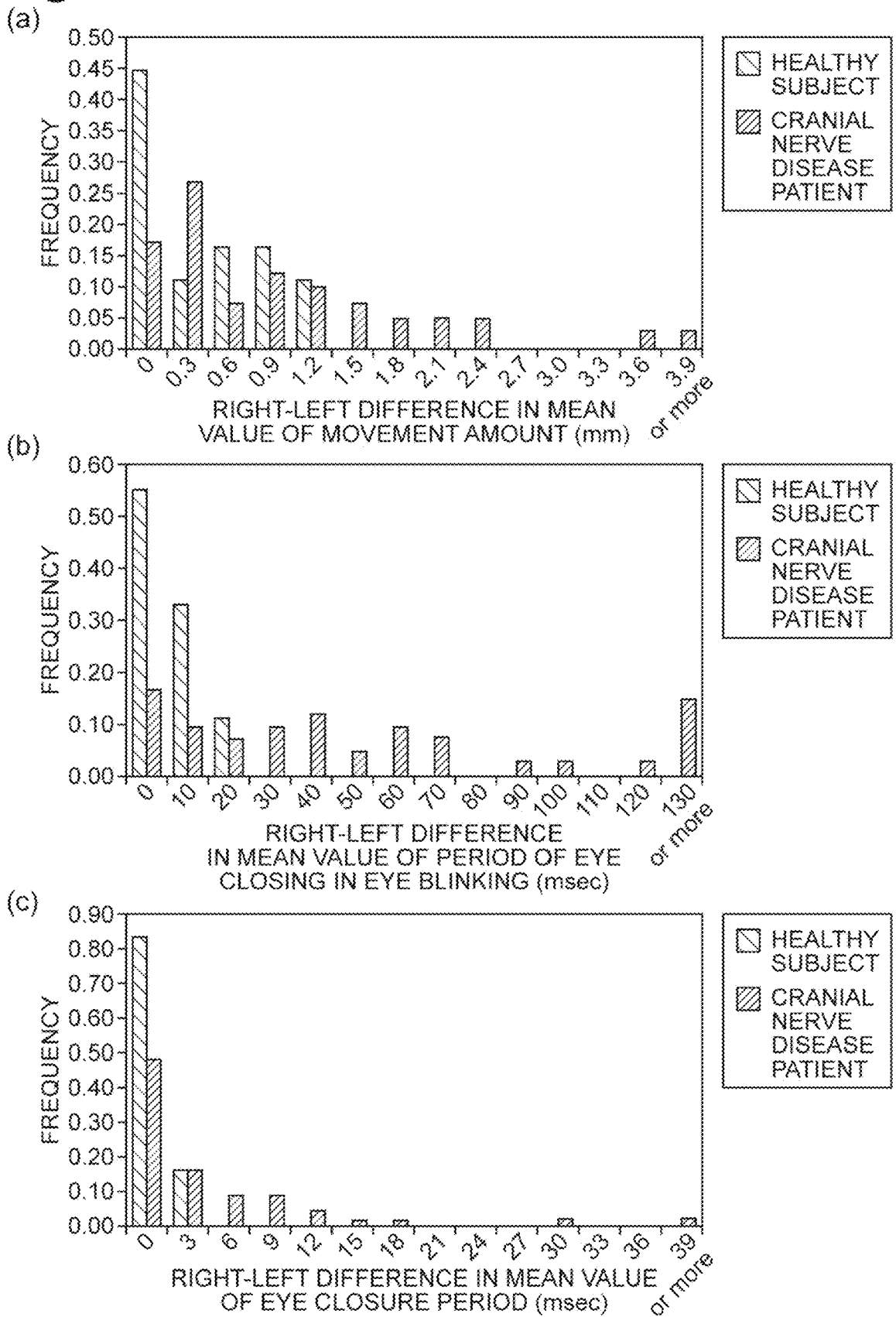
FIG. 14 are graphs showing frequencies of right-left differences in mean value of upper eyelid movement amounts at the time of eye closing in eye blinking, frequencies of right-left differences in mean value of periods of eye closing in eye blinking, and frequencies of right-left differences in mean value of eye closure periods obtained by the binocular measurement system 1 shown in FIG. 1.

FIG. 14 and FIG. 15 show examples of calculation of frequencies of right-left differences in statistics of eyeblink feature amounts of a plurality of subjects including healthy people and cranial nerve disease patients as targets. A portion (a) of FIG. 14 shows right-left differences in mean value of upper eyelid movement amounts at the time of eye closing in eye blinking, a portion (b) of FIG. 14 shows right-left differences in mean value of period of eye closing in eye blinking, a portion (c) of FIG. 14 shows right-left differences in mean value of eye closure period, a portion (a)

of FIG. 15 shows upper eyelid movement amounts at the time of eye opening in eye blinking, a portion (b) of FIG. 15 shows right-left differences in mean value of period of eye opening in eye blinking, and a portion (c) of FIG. 15 shows right-left differences in mean value of maximum speed of eye opening in eye blinking. These detection results also show that a right-left difference of a cranial nerve disease patient tends to increase as compared with a healthy person.

The present invention is not limited to the above-described embodiment.

Details to be detected of a subject by the binocular measurement system 1 described above may be other kinds.

For example, the binocular measurement system 1 may detect involuntary eye movement of a subject. A configuration of a binocular measurement system 1 according to a modification in this case will be described with a focus on differences from the above-described binocular measurement system 1.

[Configuration for Detection of Involuntary Eye Movement]

When an imaging device such as a video camera or a profile sensor is used as the photodetector 7, the binocular measurement system 1 measures a cornea reflected light, a pupil diameter, or a pupil center of a subject. When a light sensor such as a photodetector or a profile sensor is used as the photodetector 7, scleral reflected light may be measured. When detecting cornea reflected light, the feature amount calculating unit 11 of the processor 9 obtains an eyeball position by gravity center arithmetic operation on a bright spot image. The photodetector 7 or the processor 9 may calibrate a difference in movement amount caused by a difference in curvature of the cornea of a subject before measurement, or may have a function to indicate predetermined bright spots and facilitate saccade between bright spots, and reflect a correction coefficient for calibration of a movement amount. However, even during saccade detection, a subject always makes involuntary eye movement and the eyeball position when gazing at a bright spot fluctuates, so that it is also preferable to perform control to make bright spots flash, and control to continue calibration until a stable correction coefficient is obtained. For example, when a vision camera is used as the photodetector 7, an eyeball position can be calculated in real time at a predetermined frame rate while continuing acquisition of image signals of a subject, so that bright spot control and image signal acquisition may be continued until a movement width caused by saccade falls within a predetermined variation width (statistic such as a standard deviation). When detecting scleral reflected light, the photodetector 7 or the processor 9 calibrates an output value of the photosensor and an eyeball movement amount.

Figure 16:
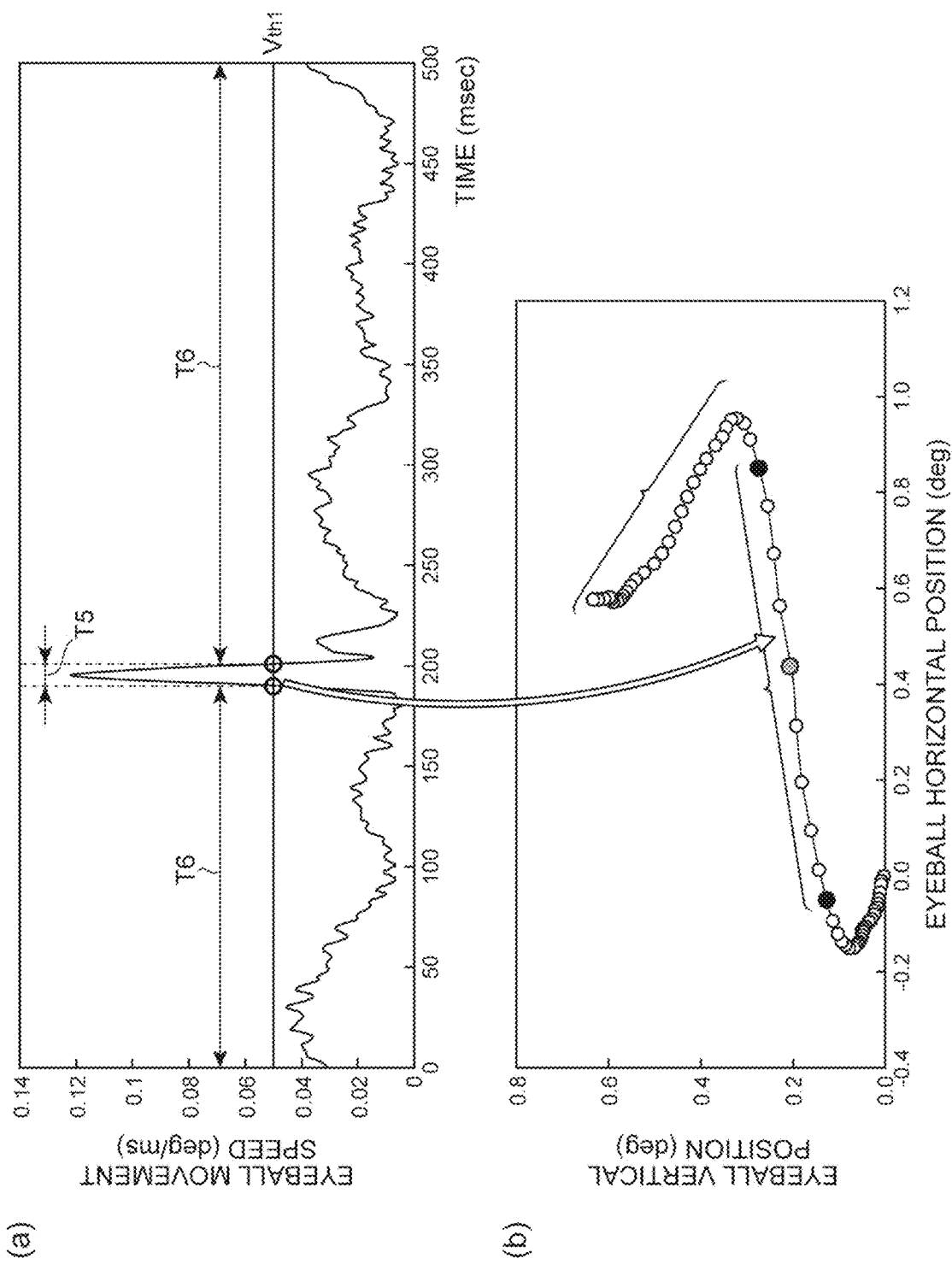
FIG. 16 are graphs showing a temporal change of an eyeball movement speed and a temporal change of an eyeball position calculated by the feature amount calculating unit 11 shown in FIG. 1.

The feature amount calculating unit 11 of the processor 9 calculates a temporal change of an eyeball position based on an image signal output from the photodetector 7. In addition, the feature amount calculating unit 11 calculates a temporal change of an eyeball position movement speed (eyeball movement speed) based on the temporal change of the eyeball position. A portion (a) of FIG. 16 shows a temporal change of an eyeball movement speed calculated by the feature amount calculating unit 11, and a portion (b) of FIG. 16 shows a temporal change of an eyeball position calculated by the feature amount calculating unit 11. Each circle shown in the portion (b) of FIG. 16 shows an eyeball position in each frame, and is calculated at time intervals of, for example, 1 millisecond. The feature amount calculating unit 11 obtains the eyeball movement speed by calculating a square root of the sum of squares of a horizontal speed and a vertical speed. The speed is obtained by first derivation of the temporal change of the eyeball position. As shown in the portion (a) of FIG. 16, a peak of the eyeball movement speed is observed according to a flick of the subject, and before and after the peak, slow movement of the eyeball position accompanying drift movement and tremor movement is detected, and as shown in the portion (b) of FIG. 16, eyeball position changes according to these movements are detected.

Figure 17:
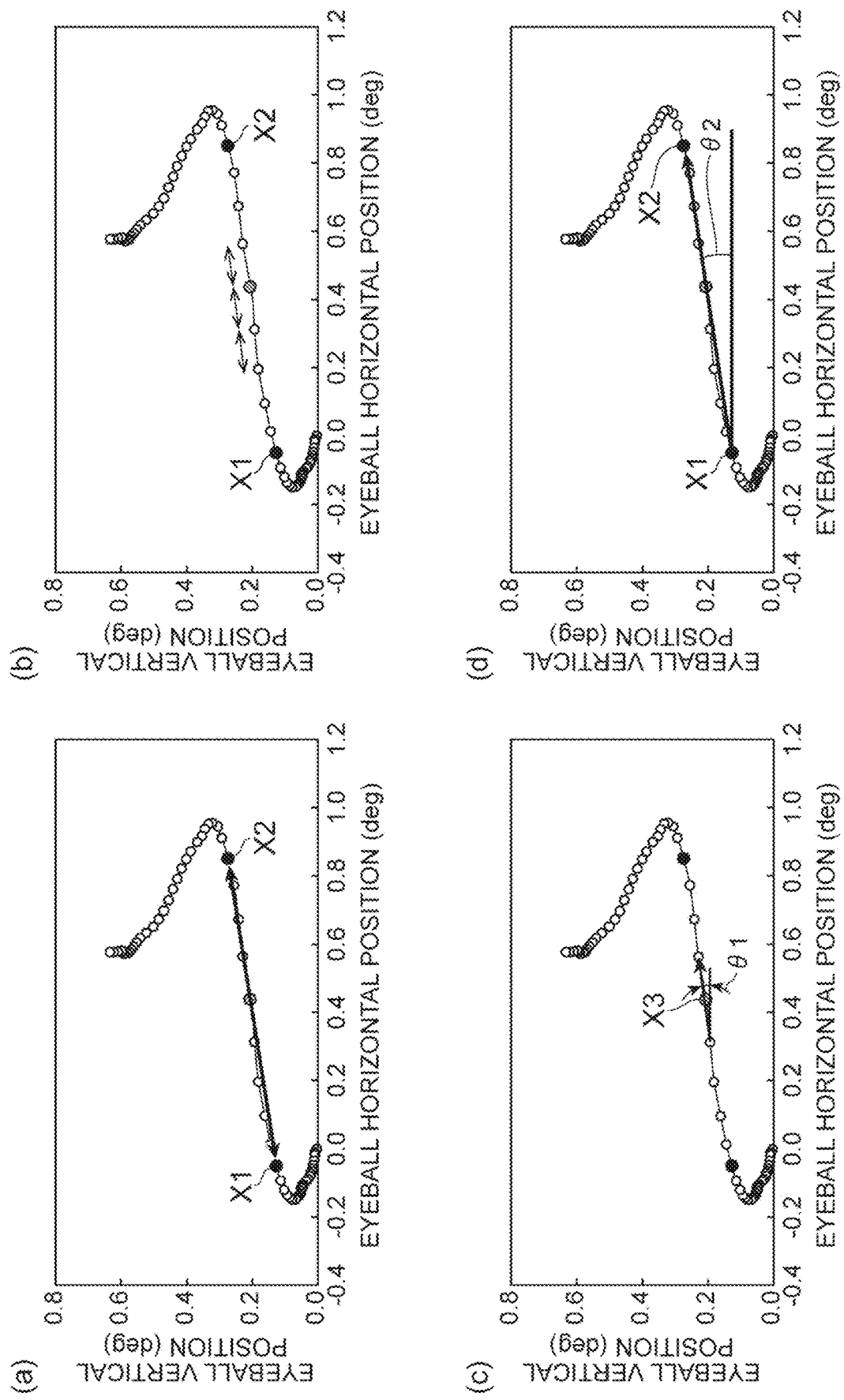
FIG. 17 are graphs showing examples of temporal changes of eyeball positions calculated by the feature amount calculating unit 11 shown in FIG. 1.

Then, based on the calculated eyeball position temporal change and eyeball movement speed temporal change, the feature amount calculating unit 11 calculates an involuntary eye movement feature amount being a feature amount related to involuntary eye movement for each of the right eye $E_R$ and the left eye $E_L$, separately. First, by comparing the temporal change of the eyeball movement speed with a speed threshold $V_{th1}$ set in advance, the feature amount calculating unit 11 identifies a period T5 in which the speed threshold $V_{th1}$ is exceeded as a flick period, and identifies the other period T6 as a period of drift movement and tremor movement. Further, the feature amount calculating unit 11 calculates, as the involuntary eye movement feature amount, a "flick period," a "flick maximum speed," a "flick start time," a "flick ending time," a "time of flick maximum speed," a "flick frequency," a "flick angle at maximum speed," an "angle of flick period," a "flick movement distance," and a "flick width" and so on. The "flick period" is calculated as a length of an observed flick period T5, the "flick maximum speed" is calculated as a maximum value of an eyeball movement speed in the flick period, the "time of flick maximum speed" is calculated as a time the maximum value is observed, and the "flick frequency" is calculated as flick occurrence frequency in a predetermined period. The "flick period" may be calculated as, for example, by using a quartile point of the flick maximum speed, a period twice as long as a half-value width of the maximum speed, may be a predetermined period before and after a section in which the speed threshold is exceeded, or may be extracted after influences of tremor and drift are reduced by applying a bypass filter to the speed waveform. As shown in a portion (a) of FIG. 17, the "flick width" is calculated as a distance between an eyeball position X1 at a flick start time and an eyeball position X2 at a flick ending time, as shown in a portion (b) of FIG. 17, the "flick movement distance" is calculated as a value obtained by summing distances between observation positions from the flick start position X1 to the flick ending position X2, as shown in a portion (c) of FIG. 17, the "flick angle at maximum speed" is calculated as an angle θ1 of a vector connecting points before and after an eyeball position X3 at a point of time a maximum speed is detected, and as shown in a portion (d) of FIG. 17, the "angle of flick period" is calculated as an angle θ2 of a vector connecting the eyeball positions X1 and X2.

Here, instead of, or in addition to the involuntary eye movement feature amount related to flick, the feature amount calculating unit 11 may calculate an involuntary eye movement feature amount related to tremor. In order to calculate a feature amount related to tremor, the feature amount calculating unit 11 extracts frequency components of 50 Hz or more from the temporal change of the eyeball position in a period except for the flick period, and calculates a feature amount based on the frequency components as targets. The feature amount calculating unit 11 calculates, as an involuntary eye movement feature amount related to tremor, a frequency feature amount and a feature amount related to an amplitude of shaking of tremor being microvibration, such as a "peak frequency by frequency analysis," a "frequency power sum of frequency analysis results," and an "amplitude," etc. The frequency analysis is "DFT (Discrete Fourier Transform)," "Wavelet analysis," or the like, and DFT may be replaced by FFT (Fast Fourier Transform). The "peak frequency" is a frequency showing a highest power value in a frequency spectrum obtained through each frequency analysis, and the "frequency power sum" is calculated as a sum of power values of the frequency spectrum in an arbitrary frequency band, and the "amplitude" is calculated as a sum of movement amounts of the eyeball position according to tremor or a movement amount in a period until the movement direction is reversed.

The feature amount calculating unit 11 may calculate an involuntary eye movement feature amount related to drift instead of, or in addition to the involuntary eye movement feature amount related to flick or tremor. When calculating feature amount related to drift, the feature amount calculating unit 11 extracts frequency components of less than 50 Hz from the temporal change of the eyeball position in a period except for the flick period, and calculates a feature amount based on the frequency components as targets. The feature amount calculating unit 11 calculates, as involuntary eye movement feature amounts related to drift, a "fractal dimension," a "peak frequency," a "frequency power sum," and an "amplitude," and so on. The "fractal dimension" is obtained by calculating a fractal dimension based on the extracted frequency components as targets, and the "peak frequency" is calculated as a peak frequency of a spectrum calculated based on the extracted frequency components, and the "amplitude" is calculated as a sum of movement amounts of the eyeball position according to drift.

Figure 18:
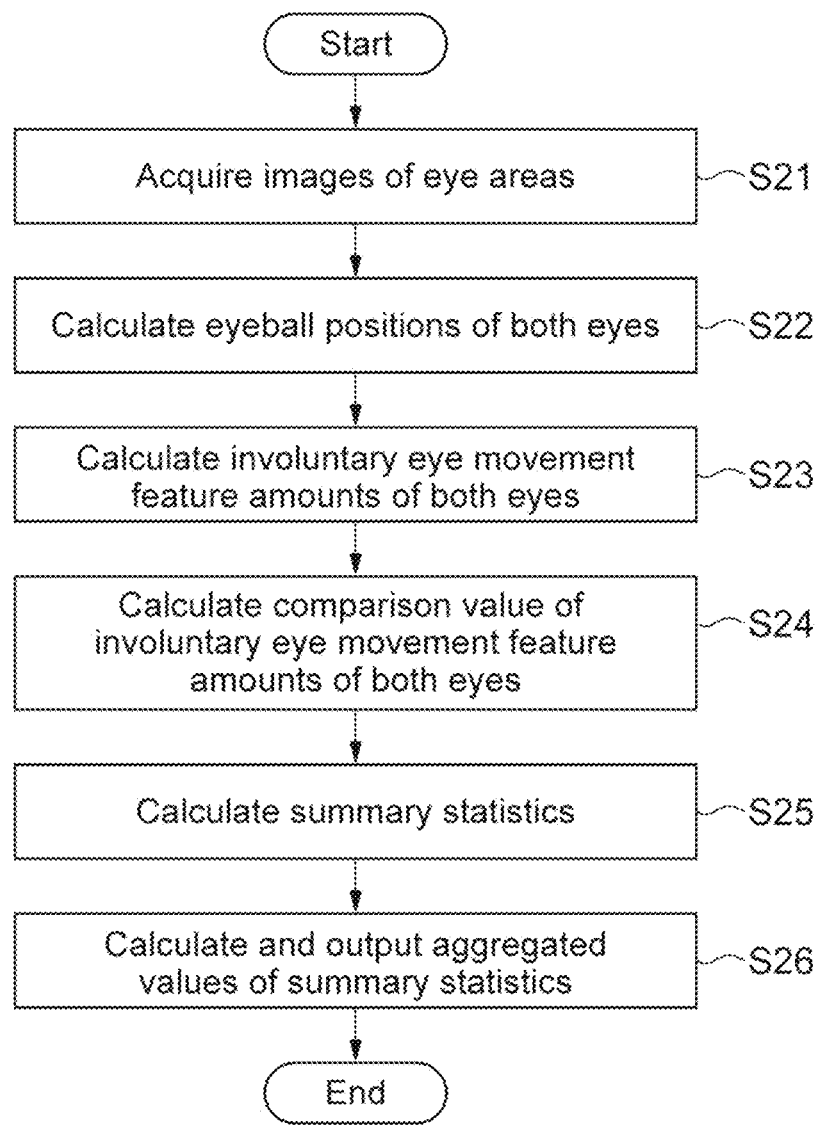
FIG. 18 is a flowchart showing steps of a comparison value measurement operation by the binocular measurement system 1 shown in FIG. 1.
Figure 19:
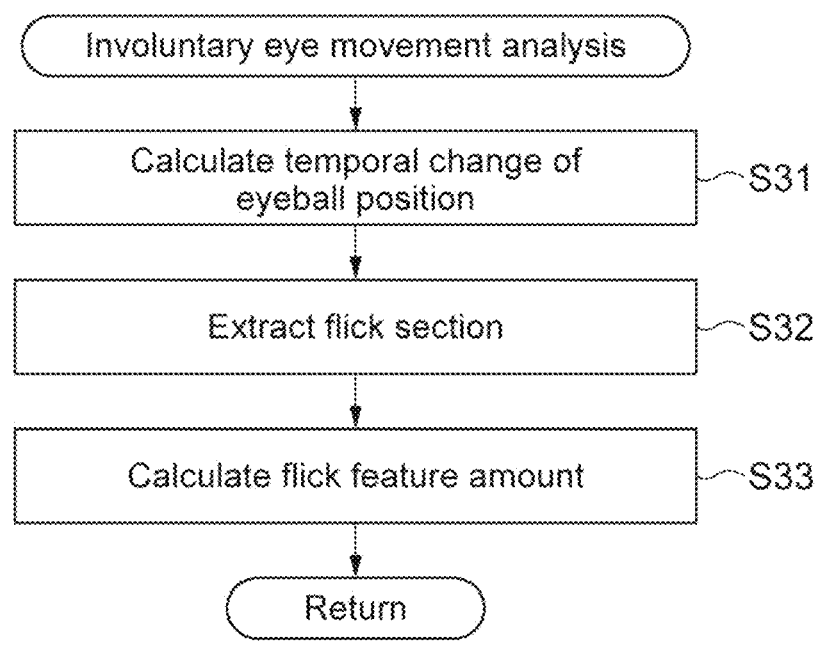
FIG. 19 is a flowchart showing detailed steps of involuntary eye movement analysis by the binocular measurement system 1 shown in FIG. 1.
Figure 20:
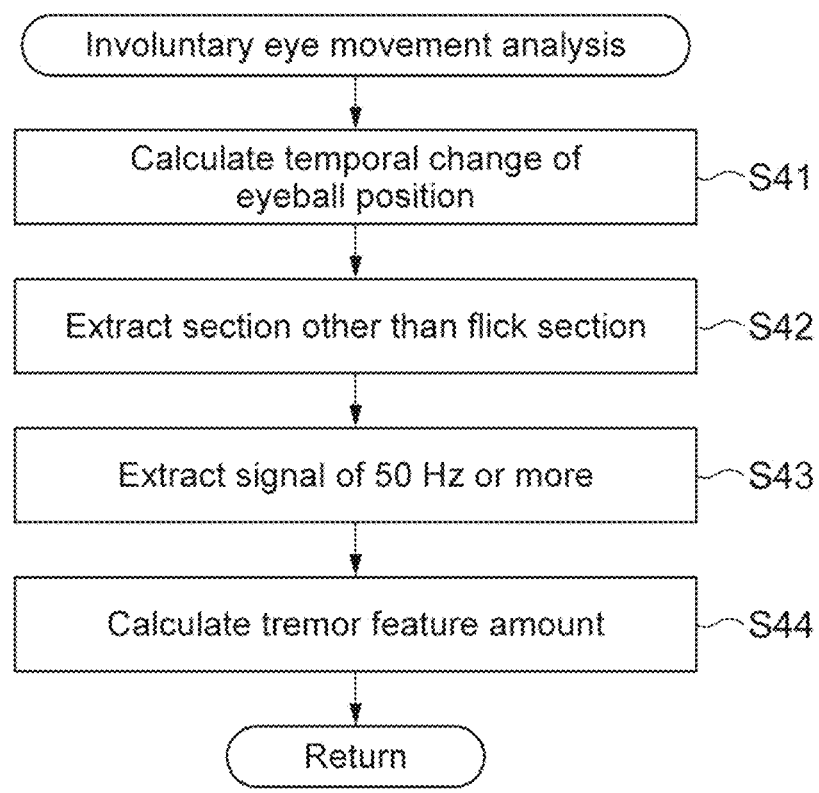
FIG. 20 is a flowchart showing detailed steps of involuntary eye movement analysis by the binocular measurement system 1 shown in FIG. 1.
Figure 21:
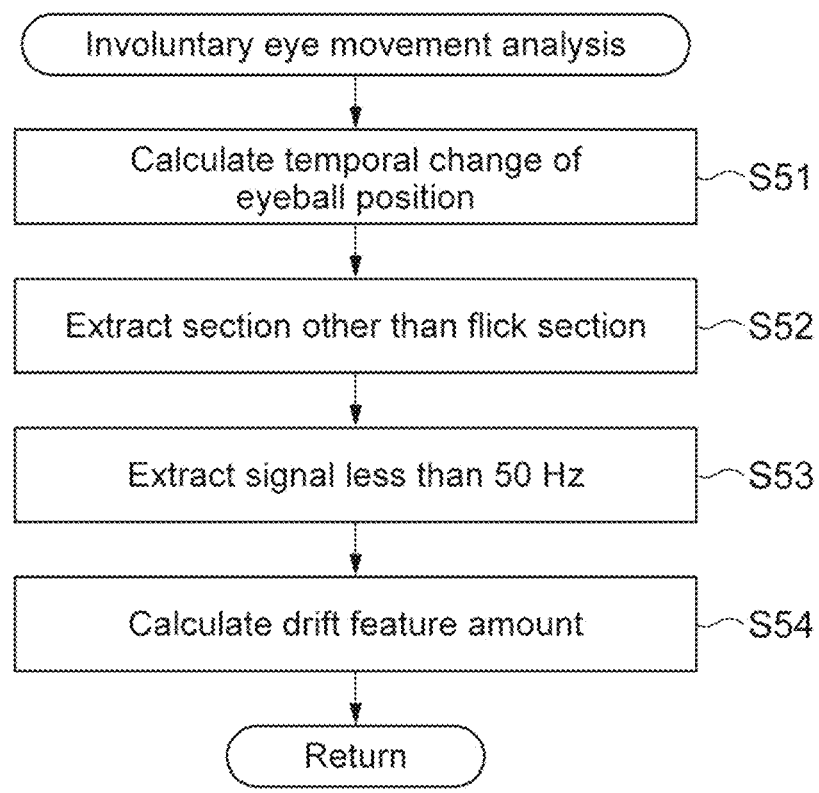
FIG. 21 is a flowchart showing detailed steps of involuntary eye movement analysis by the binocular measurement system 1 shown in FIG. 1.
Figure 22:
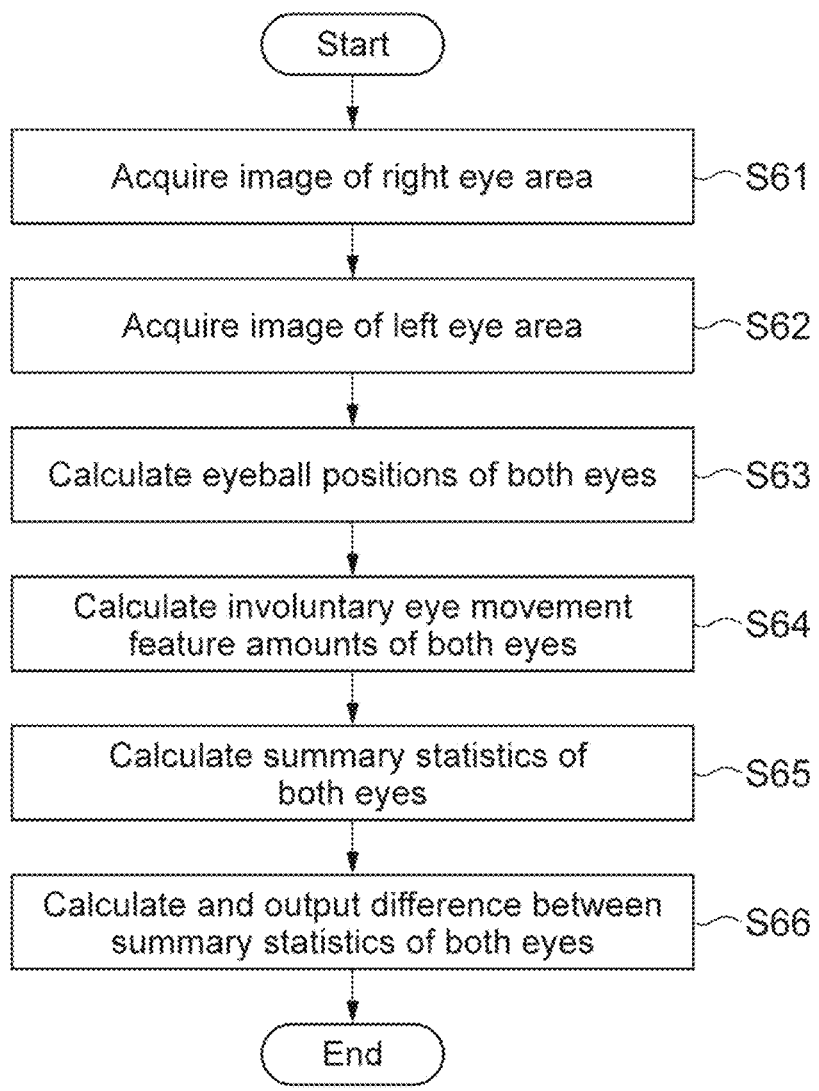
FIG. 22 is a flowchart showing steps of a comparison value measurement operation by the binocular measurement system 1 shown in FIG. 1.

FIG. 18 to FIG. 22 are flowcharts showing steps of an operation to measure a comparison value by the binocular measurement system 1. FIG. 18 shows steps of simultaneously acquiring images of the right eye $E_R$ and the left eye $E_L$ and calculating statistics based on a comparison value of involuntary eye movement feature amounts as a target, FIG. 22 shows steps of acquiring images of the right eye $E_R$ and the left eye $E_1$ separately, calculating an involuntary eye movement feature amount and a statistic thereof for each of the right eye $E_R$ and the left eye $E_L$, separately, and calculating a comparison value of the two statistics, and FIG. 19 to FIG. 21 show detailed steps of analysis of involuntary eye movement. Either one of the functions shown in FIG. 18 and FIG. 22 only needs to be implemented in the binocular measurement system 1. The steps shown in FIG. 18 and FIG. 22 are the same as the steps shown in FIG. 3 and FIG. 4 except that the processing target is an involuntary eye movement feature amount.

Referring to FIG. 19, when calculating a feature amount related to flick for each of the right eye $E_R$ and the left eye $E_L$, first, the feature amount calculating unit 11 of the processor 9 calculates a temporal change of the eyeball position (Step S31). Next, by using a temporal change of an eyeball movement speed, the feature amount calculating unit 11 detects a flick section (Step S32). Then, the feature amount calculating unit 11 calculates a feature amount related to flick by using the temporal change of the eyeball position and the temporal change of the eyeball movement speed in the flick section (Step S33).

Referring to FIG. 20, when calculating a feature amount related to tremor for each of the right eye $E_R$ and the left eye $E_L$, the feature amount calculating unit 11 of the processor 9 first calculates a temporal change of an eyeball position (Step S41). Next, the feature amount calculating unit 11 detects a flick section by using a temporal change of an eyeball movement speed, and extracts a signal of the temporal change in a section other than the flick section (step S42). Thereafter, the feature amount calculating unit 11 extracts frequency components of 50 Hz or more from the extracted signal (Step S43). Then, the feature amount calculating unit 11 calculates a feature amount related to tremor by using the extracted temporal change of the eyeball position (Step S33).

Referring to FIG. 21, when calculating a feature amount related to drift for each of the right eye $E_R$ and the left eye $E_L$, the feature amount calculating unit 11 of the processor 9 first calculates a temporal change of an eyeball position (Step S51). Next, the feature amount calculating unit 11 detects a flick section by using a temporal change of an eyeball movement speed, and extracts a signal of the temporal change in a section other than the flick section (Step S52). Thereafter, the feature amount calculating unit 11 extracts frequency components of less than 50 Hz from the extracted signal (Step S43). Then, the feature amount calculating unit 11 calculates a feature amount related to drift by using the extracted temporal change of the eyeball position (Step S33).

Also by the binocular measurement system 1 according to the modification described above, evaluation values related to behavior of the eyes of a subject can be acquired by simple calculation processing using a simple device configuration without a burden on the subject. Further, based on the evaluation values, the behavior of the eyes of the subject can be properly evaluated, and brain functions can be quantified non-invasively and easily from the behavior of the eyes.

Next, examples of measurement data obtained by the binocular measurement system 1 of the present modification are shown.

A portion (a) of FIG. 23 shows right-left differences in flick maximum speed of one subject before and after a VDT work, a portion (b) of FIG. 23 shows right-left differences in time of flick maximum speed of one subject before and after a VDT work, and a portion (c) of FIG. 23 shows right-left differences in flick maximum speed of six subjects before and after a VDT work. These results show that the right-left differences become larger and the variation in the difference is larger after the VDT work than before the VDT work.

Figure 24:
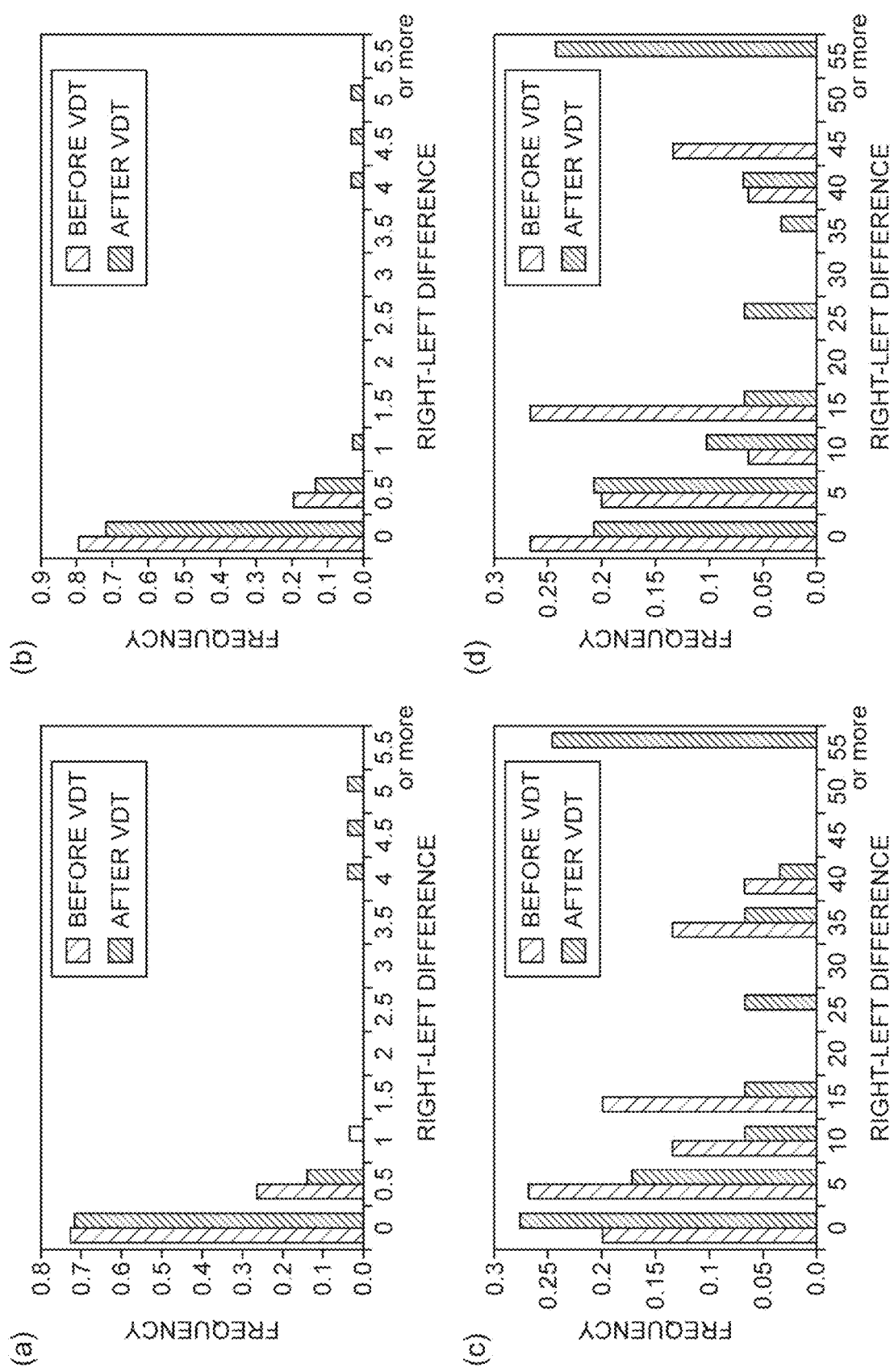
FIG. 24 are graphs showing frequency values of right-left differences in flick width, frequency values of right-left differences in flick movement distance, frequency values of right-left differences in flick angle at maximum speed, and frequency values of right-left differences in angle of flick period.

A portion (a) of FIG. 24 shows frequency values of right-left differences in flick width before and after a VDT work, a portion (b) of FIG. 24 shows frequency values of right-left differences in flick movement distance before and after a VDT work, a portion (c) of FIG. 24 shows frequency values of right-left differences in flick angle at the maximum speed before and after a VDT work, and a portion (d) of FIG. 24 shows frequency values of right-left differences in angle of flick period before and after a VDT work. These results show that the right-left differences in feature amount are larger after the VDT work.

A portion (a) of FIG. 25 shows mean values and standard deviations of right-left differences in horizontal movement frequency of tremor before and after a VDT work, and a portion (b) of FIG. 25 shows mean values and standard deviations of right-left differences in vertical movement frequency of tremor before and after a VDT work. As shown in the portion (a) of FIG. 25, it was found that the difference in horizontal movement frequency became larger and variation in the difference became larger after the VDT work than before the VDT work. As shown in the portion (b) of FIG. 25, it was found that the difference in vertical movement frequency became smaller after the VDT work than before the VDT work, however, variation in the difference became larger after the VDT work than before the VDT work.

The binocular measurement system 1 may detect the pupils of a subject. A configuration of a binocular measurement system 1 of a modification in this case will be described with a focus on differences from the binocular measurement system 1 described above.

[Configuration for Pupil Detection]

A binocular measurement system 1 of the present modification measures a pupil area or a pupil diameter or the like of a subject. That is, the feature amount calculating unit 11 of the processor 9 calculates a temporal change of a pupil area or a pupil diameter based on an image signal output from the photodetector 7.

In detail, the feature amount calculating unit 11 sets a luminance threshold for an image signal, and maintains a luminance value of a pixel with low luminance as compared with the luminance threshold, and changes a luminance value of a pixel with high luminance as compared with the luminance threshold to a predetermined value (for example, a maximum value "255") not less than the luminance threshold. As a threshold setting method in this case, a method in which an image signal is divided into small regions, a sum of luminance values is calculated in each region, and a threshold for division between a dark area group and a bright area group is adaptively obtained, a method in which a histogram of luminance values in all regions of an image signal is generated, the numbers of pixels are accumulated from the dark side, and a luminance value at which a predetermined number of pixels is satisfied is set as a threshold, a method in which a lowest luminance value of a portion higher than an eyelid position or a luminance value obtained by adding a standard deviation to a mean luminance value is set as a threshold, or a method using a fixed value, can be adopted. In this case, the feature amount calculating unit 11 may perform binarization of image processing so as to leave a pupil area. Thereafter, the feature amount calculating unit 11 removes noise other than cornea reflected light and the pupil area by applying erosion and dilation being image processing techniques a plurality of times to an image signal. A cornea reflected light part may be scattered and magnified due to influences from a tear volume on the eye surface and an intraocular lens, and in this case, it may be impossible to remove noise only by erosion and dilation. Therefore, it is preferable that the feature amount calculating unit 11 obtains the presence of a bright area in a dark area by applying labelling, etc., of image processing after the erosion and the dilation, and directly blacks out the bright area. Then, the feature amount calculating unit 11 counts the number of pixels with luminance values less than the threshold, and calculates this number as a pupil area. Further, the feature amount calculating unit 11 obtains a straight line crossing the center of gravity coordinates of cornea reflected light in the bright area in the dark area, obtains a length of intersection of the pixel group with luminance values less than the threshold obtained after the noise removal through the erosion and the dilation described above, and the straight line, and calculates this length as a pupil diameter. As another calculation method, it is also possible that a gravity center arithmetic operation is performed by using luminance information of right and left boundaries of the intersection of the pixel group and the straight line, one-dimensional coordinates of the right and left boundaries are obtained, and a distance between them is regarded as a pupil diameter, and a method in which pupil diameters obtained by applying a plurality of thresholds are averaged, may be performed.

Then, based on the calculated temporal change of the pupil diameter, the feature amount calculating unit 11 calculates a pupil feature amount being a feature amount related to the pupil for each of the right eye $E_R$ and the left eye $E_L$, separately. As the pupil feature amount, the feature amount calculating unit 11 calculates at least one of a "required time from a mydriasis peak time to a miosis peak time," a "required time from a miosis peak time to a mydriasis peak time," a "change rate from a pupil diameter and area at a mydriasis peak to a pupil diameter and area at a miosis peak," and a "change rate from a pupil diameter and area at a miosis peak to a pupil diameter and area at a mydriasis peak." A portion (a) of FIG. 26 shows an example of a temporal change of an pupil diameter calculated by the feature amount calculating unit 11, and a portion (b) of FIG. 26 shows times of mydriasis peaks and times of miosis peaks detected by the feature amount calculating unit 11. Thus, by the feature amount calculating unit 11, a time corresponding to a minimum value of the temporal change of the pupil diameter is detected as a time of a miosis peak, and a time corresponding to a maximum value of the temporal change of the pupil diameter is detected as a time of a mydriasis peak.

Figure 27:
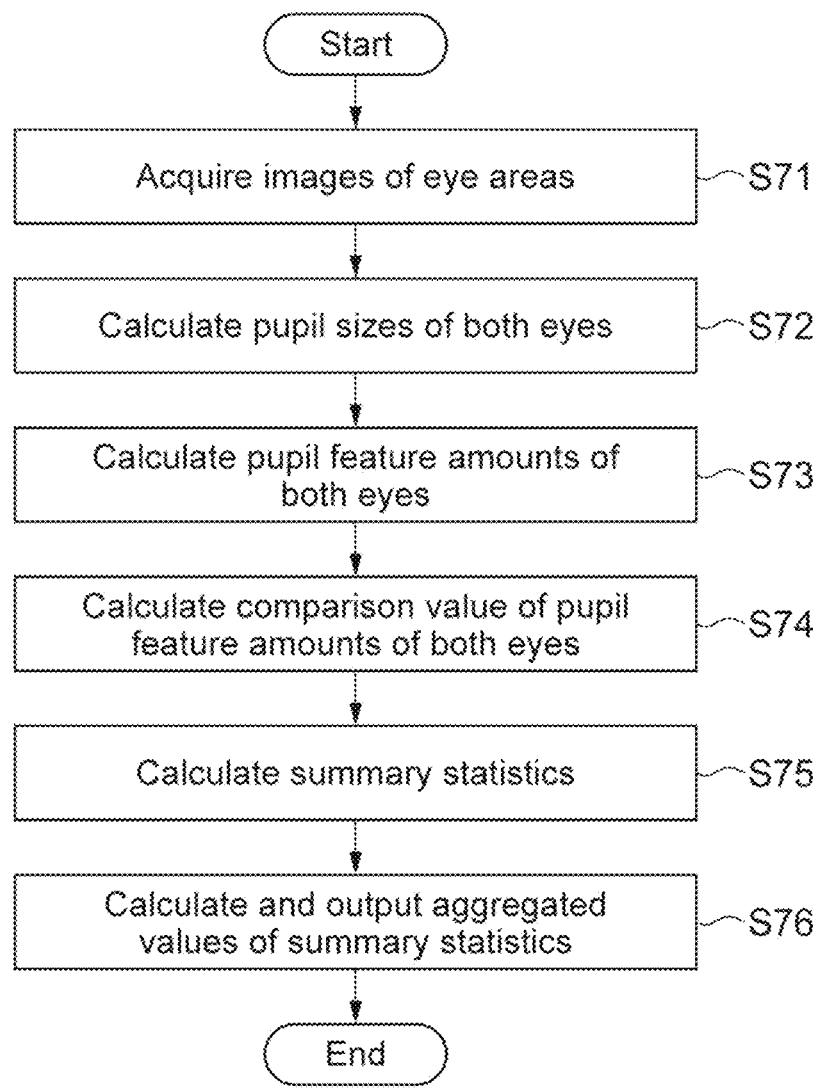
FIG. 27 is a flowchart showing steps of a comparison value measurement operation by the binocular measurement system 1 shown in FIG. 1.
Figure 28:
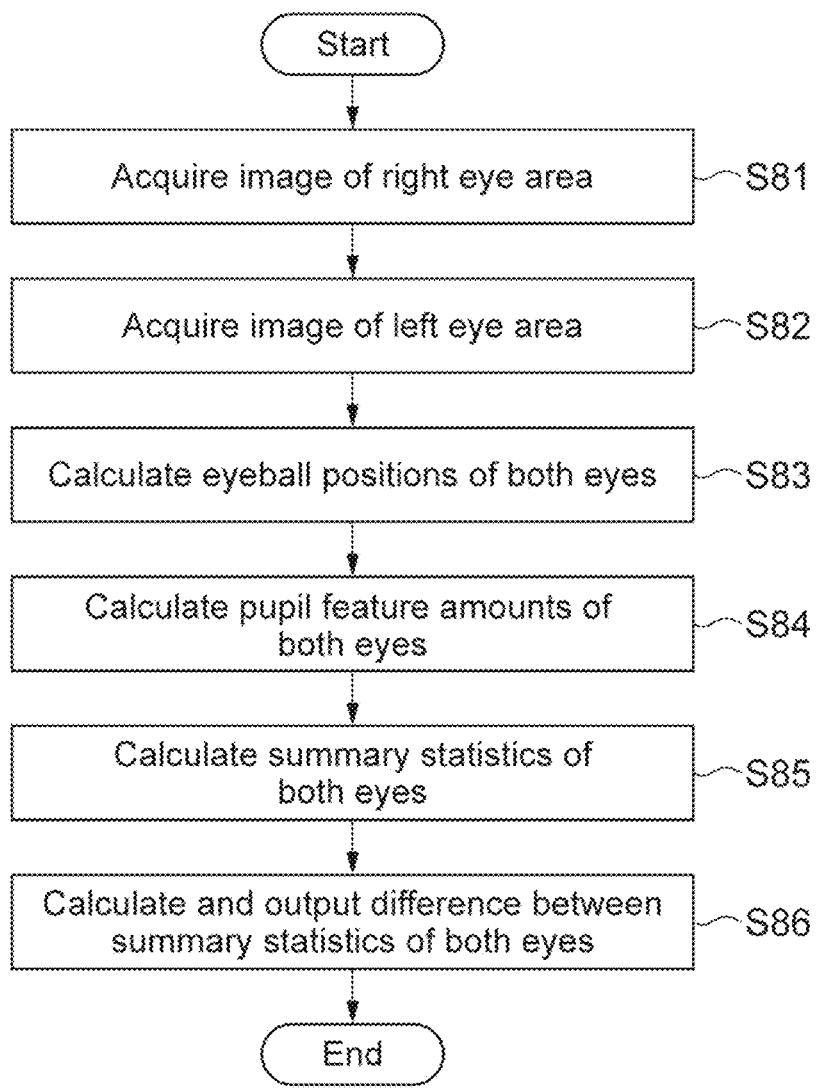
FIG. 28 is a flowchart showing steps of a comparison value measurement operation by the binocular measurement system 1 shown in FIG. 1.

FIG. 27 and FIG. 28 are flowcharts showing steps of an operation to measure a comparison value by the binocular measurement system 1. FIG. 27 shows steps of calculating statistics based on a comparison value of pupil feature amounts as a target by simultaneously acquiring images of the right eye $E_R$ and the left eye $E_L$, and FIG. 28 shows steps of acquiring images of the right eye $E_R$ and the left eye $E_L$, separately, calculating a pupil feature amount and a statistic for each of the right eye $E_R$ and the left eye $E_L$, separately, and calculating a comparison value of the two statistics. In the binocular measurement system 1, either one of the functions shown in FIG. 27 and FIG. 28 needs to be implemented. The steps shown in FIG. 27 and FIG. 28 are the same as the steps shown in FIG. 3 and FIG. 4 except that the processing targets are pupil feature amounts.

Even by the binocular measurement system 1 according to the modification described above, evaluation values related to behavior of the eyes of a subject can be acquired by a simple device configuration and simple calculation processing without a burden on the subject. Further, based on the evaluation values, the behavior of the eyes of the subject can be properly evaluated, and the brain functions can be non-invasively and easily quantified from the behavior of the eyes.

In the binocular measurement system 1 according to the embodiment described above, a difference or a ratio is calculated as a comparison value, and in this case, a section that could not be measured due to eye blinking or the like is preferably reflected in an aggregated value as an exception. In addition, when it is difficult to stably detect a pupil diameter, an area of a pupillary area or an area or a diameter resultant from ellipse approximation may be used.

As an application example of the binocular measurement system 1 according to the embodiment described above, it is expected that the system is used for diagnosis of disease conditions and for judgment of progression of a disease and follow-up after a treatment, etc., at hospitals. It is also expected that the system is used for health care for an individual person to check his/her own health, and for physiological experiments and visual experiments in laboratories.

Here, in the binocular measurement device described above, it is preferable that the comparison value calculating unit calculates a comparison value based on a difference or a ratio between a first feature amount and a second feature amount. With this configuration, behavior of the eyes of a subject can be properly evaluated by simple calculation.

Also, the feature amount calculating unit may calculate feature amounts related to eye blinking as the first feature amount and the second feature amount, may calculate feature amounts related to involuntary eye movement as the first feature amount and the second feature amount, and may calculate feature amounts related to the pupils as the first feature amount and the second feature amount. By obtaining evaluation values based on these feature amounts, behavior of both eyes of a subject can be properly evaluated.

Further, it is also preferable that the photodetector includes a two-dimensional photodetector having a light receiving surface on which a plurality of pixels are two-dimensionally arrayed. By including such a two-dimensional photodetector, feature amounts of the right eye and the left eye can be accurately obtained, and as a result, evaluation accuracy of behavior of the eyes can be improved.

INDUSTRIAL APPLICABILITY

An aspect of the present invention is used for a binocular measurement device, a binocular measurement method, and a binocular measurement program, and is to easily and properly evaluate differences in behavior of the eyes of subjects.

REFERENCE SIGNS LIST

1 . . . binocular measurement system, 3R, 3L . . . light source, 5 . . . lighting control device, 7 . . . photodetector, 9 . . . processor, 11 . . . feature amount calculating unit, 13 . . . comparison value calculating unit, 15 . . . result output unit, 17 . . . synchronous control unit, $E_L$ . . . left eye, $E_R$ . . . right eye

The invention claimed is:

1. A binocular measurement device comprising:
a photodetector configured to detect light from a right eye and a left eye of a target person, and output a detection signal; and
a processor electrically coupled to the photodetector and configured to input the detection signal, wherein
the processor is configured to:
calculate a first feature amount corresponding to the right eye and a second feature amount corresponding to the left eye based on the detection signal; and
calculate, based on feature amounts of the first feature amount and the second feature amount, a comparison value obtained by comparing the first feature amount and the second feature amount,
wherein the processor calculates feature amounts related to eye blinking as the first feature amount and the second feature amount, and
wherein the processor calculates the feature amounts related to eye blinking by
(i) calculating a temporal change of an upper eyelid position and a temporal change of an upper eyelid movement speed for each of the right eye and the left eye, separately, and
(ii) calculating the feature amount related to eye blinking for each of the right eye and the left eye, separately, based on the calculated temporal change of the upper eyelid position and the calculated temporal change of the upper eyelid movement speed.

2. The binocular measurement device according to claim 1, wherein
the processor is configured to calculate a comparison value based on a difference or a ratio between the first feature amount and the second feature amount.

3. The binocular measurement device according to claim 1, wherein
the processor is configured to calculate feature amounts related to the pupils as the first feature amount and the second feature amount.

4. The binocular measurement device according to claim 1, wherein
the photodetector includes a two-dimensional photodetector having a light receiving surface on which a plurality of pixels are two-dimensionally arrayed.

5. A binocular measurement device comprising:
a photodetector configured to detect light from a right eye and a left eye of a target person, and output a detection signal; and
a processor electrically coupled to the photodetector and configured to input the detection signal, wherein
the processor is configured to:
calculate a first feature amount corresponding to the right eye and a second feature amount corresponding to the left eye based on the detection signal; and
calculate, based on feature amounts of the first feature amount and the second feature amount, a comparison value obtained by comparing the first feature amount and the second feature amount,
wherein the processor calculates feature amounts related to involuntary eye movement as the first feature amount and the second feature amount, and
wherein the processor calculates the feature amounts related to involuntary eye movement by
(i) calculating a temporal change of an eyeball position movement speed for each of the right eye and the left eye, separately,
(ii) comparing the temporal change of the eyeball position movement speed for each of the right eye and the left eye with a predetermined threshold,
(iii) identifying, for each of the right eye and the left eye, separately, a period in which the threshold is exceeded by the temporal change of the eyeball position movement speed as a period of a flick, and a period in which the threshold is not exceeded by the temporal change of the eyeball position movement speed as a period of drift movement and tremor movement, and
(iv) calculating, for each of the right eye and the left eye, separately, one or more feature amounts of the flick, the drift movement, and the tremor movement, as the feature amount related to involuntary eye movement.

6. The binocular measurement device according to claim 5, wherein
the processor is configured to calculate a comparison value based on a difference or a ratio between the first feature amount and the second feature amount.

7. The binocular measurement device according to claim 5, wherein
the photodetector includes a two-dimensional photodetector having a light receiving surface on which a plurality of pixels are two-dimensionally arrayed.

* * * * *